US012721871B2

(12) United States Patent
Flamand et al.

(10) Patent No.: US 12,721,871 B2
(45) Date of Patent: Sep. 1, 2026

(54) PROBIOTICS FOR THE PREVENTION OR TREATMENT OF VIRAL RESPIRATORY INFECTIONS

(71) Applicants: Université Libre de Bruxelles, Brussels (BE); SUPERBIOTICS SRL, Eghezée (BE)

(72) Inventors: Véronique Lucie Andrée Flamand, Brussels (BE); Jehan Liénart, Pommerloch (LU); France Fannes, Waterloo (BE)

(73) Assignees: Université Libre de Bruxelles, Brussels (BE); SUPERBIOTICS SRL, Eghezée (BE)

( * ) Notice: Subject to any disclaimer, the term of this patent is extended or adjusted under 35 U.S.C. 154(b) by 0 days.

(21) Appl. No.: 18/861,561

(22) PCT Filed: Apr. 28, 2023

(86) PCT No.: PCT/EP2023/061384

§ 371 (c)(1),
(2) Date: Oct. 29, 2024

(87) PCT Pub. No.: WO2023/209224

PCT Pub. Date: Nov. 2, 2023

(65) Prior Publication Data

US 2025/0170192 A1 May 29, 2025

(30) Foreign Application Priority Data

Apr. 29, 2022 (EP) .................................... 22170935

(51) Int. Cl.

| | |
|---|---|
| ***A61K 35/747*** | (2015.01) |
| ***A61K 35/00*** | (2006.01) |
| ***A61K 35/745*** | (2015.01) |
| ***A61P 31/14*** | (2006.01) |
| ***A61P 31/16*** | (2006.01) |

(52) U.S. Cl.
CPC .......... *A61K 35/747* (2013.01); *A61K 35/745* (2013.01); *A61P 31/14* (2018.01); *A61P 31/16* (2018.01); *A61K 2035/115* (2013.01)

(58) Field of Classification Search
None
See application file for complete search history.

(56) References Cited

U.S. PATENT DOCUMENTS

| | | | |
|---|---|---|---|
| 11,026,913 B2 * | 6/2021 | Morris ................... | A61K 45/06 |
| 2012/0201798 A1 * | 8/2012 | Kekkonen .............. | A61P 43/00 435/252.9 |
| 2016/0354418 A1 * | 12/2016 | Quintens ............. | A61K 35/745 |
| 2019/0000895 A1 * | 1/2019 | Lienart Van Lidth De Jeude ....... | A61K 9/1075 |

FOREIGN PATENT DOCUMENTS

| | | |
|---|---|---|
| ES | 2551053 B1 | 9/2016 |
| WO | 2006/007526 A1 | 1/2006 |

OTHER PUBLICATIONS

International Search Report issued in corresponding PCT Application No. PCT/EP2023/061384, mailed on Jul. 17, 2023 (6 pages).
Written Opinion issued in corresponding International Patent Application No. PCT/EP2023/061384, mailed on Jul. 17, 2023 (19 pages).
International Preliminary Report on Patentability issued in corresponding International Patent Application No. PCT/EP2023/061384, mailed on Aug. 6, 2024 (14 pages).
Williams Lily M et al, "The Effects of Prebiotics, Synbiotics, and Short-Chain Fatty Acids on Respiratory Tract Infections and Immune Function: A Systematic Review and Meta-Analysis", United States vol. 13, No. 1,Feb. 1, 2022 (Feb. 1, 2022), p. 167-192, Advances in Nutrition (26 pages).
Kukkonen Kaarina et al, "Long-term safety and impact on infection rates of postnatal probiotic and prebiotic (synbiotic) treatment: Randomized, double-blind, placebo-controlled trial", Pediatrics, American Academy of Pediatrics, US, vol. 122, No. 1, Jul. 1, 2008 (Jul. 1, 2008), p. 8-12 (6 pages).
Sanz Yolanda, "Gut microbiota and probiotics in maternal and infant health", American Journal of Clinical Nutrition,, vol. 94, No. 6, Dec. 1, 2011 (Dec. 1, 2011), p. 2000S-2005S (6 pages).

* cited by examiner

*Primary Examiner* — Vera Afremova
(74) *Attorney, Agent, or Firm* — Osha Bergman Watanabe & Burton LLP

(57) ABSTRACT

This invention relates to the field of probiotics. In particular, the invention relates to a composition comprising a probiotic for use in the prevention or treatment of a viral respiratory infection in a subject, wherein said composition is administered to the subject's pregnant or lactating mother, wherein said probiotic comprises a *Lactobacillus rhamnosus* strain and/or a *Bifidobacterium animalis* spp *lactis* strains, and related methods and uses and compositions for use in these methods.

17 Claims, 11 Drawing Sheets

Specification includes a Sequence Listing.

A

Lungs : cDCs 1

$CD45^+CD64^-Lin^-MHCII^+CD11c^+CD26^+XCR1^+SIRP\alpha^-$

B

Lungs : cDCs 1

$CD45^+CD64^-Lin^-MHCII^+CD11c^+CD26^+XCR1^+SIRP\alpha^-$

A

B

C

D

E

F

A

B

C

D

A

B

C

A

B

C

D

E

F

SEQUENCE LISTING

```
Sequence total quantity: 24
SEQ ID NO: 1            moltype = DNA  length = 23
FEATURE                 Location/Qualifiers
source                  1..23
                        mol_type = other DNA
                        note = influenza A virus sense primer
                        organism = synthetic construct
SEQUENCE: 1
aagaccaatc ctgtcacctc tga                                         23

SEQ ID NO: 2            moltype = DNA  length = 22
FEATURE                 Location/Qualifiers
source                  1..22
                        mol_type = other DNA
                        note = influenza A virus antisense primer
                        organism = synthetic construct
SEQUENCE: 2
caaagaccaa tcctgtcagt cc                                          22

SEQ ID NO: 3            moltype = DNA  length = 20
FEATURE                 Location/Qualifiers
source                  1..20
                        mol_type = other DNA
                        note = influenza A virus probe
                        organism = synthetic construct
SEQUENCE: 3
tttgtgttca cgctcaccgt                                             20
```

```
SEQ ID NO: 4            moltype = DNA  length = 21
FEATURE                 Location/Qualifiers
source                  1..21
                        mol_type = other DNA
                        note = PVM SH sense primer
                        organism = synthetic construct
SEQUENCE: 4
gcctgcatca acacagtgtg t                                          21

SEQ ID NO: 5            moltype = DNA  length = 19
FEATURE                 Location/Qualifiers
source                  1..19
                        mol_type = other DNA
                        note = PVM SH antisense primer
                        organism = synthetic construct
SEQUENCE: 5
gcctgatgtg gcagtgctt                                             19

SEQ ID NO: 6            moltype = DNA  length = 21
FEATURE                 Location/Qualifiers
source                  1..21
                        mol_type = other DNA
                        note = PVM SH probe
                        organism = synthetic construct
SEQUENCE: 6
cgctgataat ggcctgcagc a                                          21

SEQ ID NO: 7            moltype = DNA  length = 20
FEATURE                 Location/Qualifiers
source                  1..20
                        mol_type = other DNA
                        note = m-PPIA forward primer
                        organism = synthetic construct
SEQUENCE: 7
tcctggcatc ttgtccatgg                                            20

SEQ ID NO: 8            moltype = DNA  length = 20
FEATURE                 Location/Qualifiers
source                  1..20
                        mol_type = other DNA
                        note = m-PPIA reverse primer
                        organism = synthetic construct
SEQUENCE: 8
ttgccatcca gccattcagt                                            20

SEQ ID NO: 9            moltype = DNA  length = 30
FEATURE                 Location/Qualifiers
source                  1..30
                        mol_type = other DNA
                        note = m-PPIA probe
                        organism = synthetic construct
SEQUENCE: 9
tgctggacca aacacaaacg gcggttccca                                 30

SEQ ID NO: 10           moltype = DNA  length = 21
FEATURE                 Location/Qualifiers
source                  1..21
                        mol_type = other DNA
                        note = m-HPRT forward primer
                        organism = synthetic construct
SEQUENCE: 10
ggacctctcg aagtgttgga t                                          21

SEQ ID NO: 11           moltype = DNA  length = 22
FEATURE                 Location/Qualifiers
source                  1..22
                        mol_type = other DNA
                        note = m-HPRT reverse primer
                        organism = synthetic construct
SEQUENCE: 11
ccaacaacaa acttgtctgg aa                                         22

SEQ ID NO: 12           moltype = DNA  length = 25
FEATURE                 Location/Qualifiers
source                  1..25
                        mol_type = other DNA
                        note = m-HPRT probe
                        organism = synthetic construct
```

```
SEQUENCE: 12
caggccagac tttgttggat ttgaa                                            25

SEQ ID NO: 13          moltype = DNA  length = 21
FEATURE                Location/Qualifiers
source                 1..21
                       mol_type = other DNA
                       note = m-IFNgamma forward primer
                       organism = synthetic construct
SEQUENCE: 13
ggatgcattc atgagtattg c                                                21

SEQ ID NO: 14          moltype = DNA  length = 19
FEATURE                Location/Qualifiers
source                 1..19
                       mol_type = other DNA
                       note = m-IFNgamma reverse primer
                       organism = synthetic construct
SEQUENCE: 14
gcttcctgag gctggattc                                                   19

SEQ ID NO: 15          moltype = DNA  length = 26
FEATURE                Location/Qualifiers
source                 1..26
                       mol_type = other DNA
                       note = m-IFNgamma probe
                       organism = synthetic construct
SEQUENCE: 15
tttgaggtca acaacccaca ggtcca                                           26

SEQ ID NO: 16          moltype = DNA  length = 23
FEATURE                Location/Qualifiers
source                 1..23
                       mol_type = other DNA
                       note = m-Cxcl9 forward primer
                       organism = synthetic construct
SEQUENCE: 16
gaaccctagt gataaggaat gca                                              23

SEQ ID NO: 17          moltype = DNA  length = 23
FEATURE                Location/Qualifiers
source                 1..23
                       mol_type = other DNA
                       note = m-Cxcl9 reverse primer
                       organism = synthetic construct
SEQUENCE: 17
ctgtttgagg tctttgaggg att                                              23

SEQ ID NO: 18          moltype = DNA  length = 22
FEATURE                Location/Qualifiers
source                 1..22
                       mol_type = other DNA
                       note = m-Cxcl9 probe
                       organism = synthetic construct
SEQUENCE: 18
catcagcacc agccgaggca cg                                               22

SEQ ID NO: 19          moltype = DNA  length = 20
FEATURE                Location/Qualifiers
source                 1..20
                       mol_type = other DNA
                       note = m-Cxcl10 forward primer
                       organism = synthetic construct
SEQUENCE: 19
gccgtcattt tctgcctcat                                                  20

SEQ ID NO: 20          moltype = DNA  length = 20
FEATURE                Location/Qualifiers
source                 1..20
                       mol_type = other DNA
                       note = m-Cxcl10 reverse primer
                       organism = synthetic construct
SEQUENCE: 20
gcttccctat ggccctcatt                                                  20

SEQ ID NO: 21          moltype = DNA  length = 21
FEATURE                Location/Qualifiers
source                 1..21
                       mol_type = other DNA
```

-continued

```
                      note = m-Cxcl10 probe
                      organism = synthetic construct
SEQUENCE: 21
tctcgcaagg acggtccgct g                                             21

SEQ ID NO: 22         moltype = DNA  length = 25
FEATURE               Location/Qualifiers
source                1..25
                      mol_type = other DNA
                      note = m-Eomes forward primer
                      organism = synthetic construct
SEQUENCE: 22
ccttcacctt ctcagagaca cagtt                                         25

SEQ ID NO: 23         moltype = DNA  length = 24
FEATURE               Location/Qualifiers
source                1..24
                      mol_type = other DNA
                      note = m-Eomes reverse primer
                      organism = synthetic construct
SEQUENCE: 23
tcgatcttta gctgggtgat atcc                                          24

SEQ ID NO: 24         moltype = DNA  length = 24
FEATURE               Location/Qualifiers
source                1..24
                      mol_type = other DNA
                      note = m-Eomes probe
                      organism = synthetic construct
SEQUENCE: 24
tcgctgtgac ggcctaccaa aaca                                          24
```

PROBIOTICS FOR THE PREVENTION OR TREATMENT OF VIRAL RESPIRATORY INFECTIONS

This application contains a sequence listing in computer readable form (File name: "ULB-122-PCT.xml"; date of creation: Apr. 24, 2023; File size: 25.8 kilobytes), which is incorporated herein by reference in its entirety and forms part of the disclosure.

BIOLOGICAL DEPOSIT

Representative substances of the present invention were deposited with the Belgian Coordinated Collections of Microorganisms ("BCCM"), Laboratorium voor Microbiologie—Bacterienverzameling (LMG), Ghent University, K. L. Ledeganckstraat 35, 9000 Ghent, Belgium, on Jan. 27, 2014. The original deposit on Jan. 27, 2014, was made under reference number VES001-LMG S-28148, and on Apr. 27, 2023, a request to convert the original deposit to a deposit under the Budapest Treaty was filed. Upon conversion to a deposit under the Budapest Treaty, the deposit was given Accession number BCCM/MG P-33100. The deposit under Accession number BCCM/MG P-33100 contains a *Lactobacillus rhamnosus* strain.

FIELD OF THE INVENTION

The invention is broadly in the field of probiotics. In particular, the invention pertains to probiotics useful for the prevention or treatment of viral respiratory infections in subjects, and to related compositions, methods and uses.

BACKGROUND OF THE INVENTION

Respiratory infections are extremely common, especially among infants and young children because of their weak conditions and immature immune defenses (e.g. their respiratory tract is not yet strong in fighting off these infections and/or inflammations). In the first year of life, infants may be prone to recurrent respiratory infections, often experiencing between three and six infections during that year alone. Children miss school days due to illness, and often a parent misses work to stay home and care for the sick infant or child.

Respiratory infections and their symptoms can range from mild to severe, sometimes requiring hospitalization, depending on the type of virus causing the infection and the location of the infection. Upper respiratory infections often manifest themselves as common colds, causing inflammation and swelling of the lining of the nose, throat and sinuses. Influenza, commonly known as the flu, is a highly contagious viral infection of the upper respiratory tract. Symptoms of the flu include fever, chills, headache, muscle aches, dizziness, cough, sore throat, runny nose, nausea and diarrhea. Another upper respiratory infection, croup, causes a very deep cough and varying degrees of breathing difficulty, primarily when inhaling. Lower respiratory infections are generally considered more serious than upper respiratory infections. Bronchitis is a lower respiratory infection that affects the bronchial tubes, causing narrowing and swelling due to viral inflammation. Bronchiolitis is similar to bronchitis, but occurs primarily in infants. It is an inflammation of the smaller tubes of the branching network of bronchi. The infection causes labored breathing, frequent and dramatic coughing and wheezing and may require hospitalization. Pneumonia is caused by an infection in the alveoli, causing them to become filled with fluid, often of a thick purulent nature, that interferes with proper exchange of carbon dioxide. Pneumonia is probably the most serious lower respiratory infection for infants and children; the severity of the pneumonia will depend on the amount of lung tissue involved.

Most upper and lower respiratory infections are caused by viruses, for which no specific prevention or treatment is currently available. Some respiratory infections, including influenza, may be prevented with a vaccination. However, even when vaccinations are developed for specific respiratory infections, they are expensive and not universally available. Further, the rapidly changing nature of certain viruses due to viral mutagenesis can make effective vaccination difficult. Anti-viral drugs have so far had only limited utility. They can be effective against some, but not all, viruses. Moreover, treatment with these drugs often requires pulmonary administration, which can lead to significant stress in young infants.

Probiotics have been investigated for their ability to prevent and treat respiratory infections in humans, including children. For instance, WO2006007526 A1 reports on a composition of *Lactobacillus rhamnosus* GG and *Bifidobacterium animalis* subsp. *lactis* for use in the treatment of respiratory infections in infants. These compositions are administered to the children. However, oral supplementation may not be convenient for infants and young children.

Hence, there remains a need in the art for compositions and methods for the prevention and treatment of viral respiratory infections especially in infants and children, which are low-cost, easy to administer without imposing stress on infants and children and readily accessible.

SUMMARY OF THE INVENTION

The present inventors unexpectedly demonstrated that maternal probiotic intervention during pregnancy and/or lactation reduces the risk of a viral respiratory infection in the progeny. In particular, they found reduced viral loads in the respiratory tract of progeny infected with influenza virus H1N1 strain from mothers that were administered a probiotic, in particular *Lactobacillus rhamnosus* or *Bifidobacterium animalis* spp *lactis*, during pregnancy and lactation relative to progeny of mothers not treated with the probiotic, who were exposed to the same viral threat.

Accordingly, the present invention provides aspects and embodiments as set forth in the following Statements:

Statement 1. A composition for maternal administration comprising a probiotic, wherein said probiotic comprises or consists of *Lactobacillus rhamnosus* VES001 and/or *Bifidobacterium animalis* spp *lactis* VES002 (as deposited with the BCCM/LMG under the accession number LMG P-28149 on Jan. 27, 2014), preferably wherein said probiotic consists of *Lactobacillus rhamnosus* VES001 or *Bifidobacterium animalis* spp *lactis* VES002 (as deposited with the BCCM/LMG under the accession number LMG P-28149 on Jan. 27, 2014).

Statement 2. Use of a probiotic as a supplement in a maternal diet, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain, preferably wherein said probiotic consists of a *Lactobacillus rhamnosus* strain, or a *Lactobacillus johnsonii* strain, or a *Bifidobacterium animalis* spp *lactis* strain, or a *Lactobacillus rhamnosus* strain and a *Bifidobacterium animalis* spp *lactis* strain.

Statement 3. Use according to statement 2, wherein said probiotic is comprised in a composition.

Statement 4. Use according to statement 2 or 3, wherein the maternal diet is supplemented during pregnancy and/or during lactating.

Statement 5. Non-therapeutic use of a composition comprising an effective amount of a probiotic for improving immunity in a subject, wherein said composition is administered to the subject's pregnant or lactating mother, and wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain, preferably wherein said probiotic consists of a *Lactobacillus rhamnosus* strain, or a *Lactobacillus johnsonii* strain, or a *Bifidobacterium animalis* spp *lactis* strain, or a *Lactobacillus rhamnosus* strain and a *Bifidobacterium animalis* spp *lactis* strain.

Statement 6. Use of a probiotic in the manufacturing of a composition, preferably a food composition, for administration to a pregnant or lactating mother for improving immunity in the offspring, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain, preferably wherein said probiotic consists of a *Lactobacillus rhamnosus* strain, or a *Lactobacillus johnsonii* strain, or a *Bifidobacterium animalis* spp *lactis* strain, or a *Lactobacillus rhamnosus* strain and a *Bifidobacterium animalis* spp *lactis* strain.

Statement 7. A method for improving immunity in a subject, said method comprising the administration of a composition comprising an effective amount of a probiotic to the subject's pregnant or lactating mother, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain, preferably wherein said probiotic consists of a *Lactobacillus rhamnosus* strain, or a *Lactobacillus johnsonii* strain, or a *Bifidobacterium animalis* spp *lactis* strain, or a *Lactobacillus rhamnosus* strain and a *Bifidobacterium animalis* spp *lactis* strain.

Statement 8. A composition comprising an effective amount of a probiotic for use in improving immunity in a subject, wherein said composition is administered to the subject's pregnant or lactating mother, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain, preferably wherein said probiotic consists of a *Lactobacillus rhamnosus* strain, or a *Lactobacillus johnsonii* strain, or a *Bifidobacterium animalis* spp *lactis* strain, or a *Lactobacillus rhamnosus* strain and a *Bifidobacterium animalis* spp *lactis* strain.

Statement 9. Use of a probiotic in the manufacturing of a medicament or pharmaceutical composition for administration to a pregnant or lactating mother for improving immunity in the offspring, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain, preferably wherein said probiotic consists of a *Lactobacillus rhamnosus* strain, or a *Lactobacillus johnsonii* strain, or a *Bifidobacterium animalis* spp *lactis* strain, or a *Lactobacillus rhamnosus* strain and a *Bifidobacterium animalis* spp *lactis* strain.

Statement 10. The composition for use according to statement 8, use according to any one of statements 5, 6 or 9, or the method according to statement 7, wherein said probiotic comprises or consists of *Lactobacillus rhamnosus* VES001 and/or *Bifidobacterium animalis* spp *lactis* VES002 as deposited with the BCCM/LMG under the accession number LMG P-28149 on Jan. 27, 2014, preferably wherein said probiotic consists of *Lactobacillus rhamnosus* VES001 or *Bifidobacterium animalis* spp *lactis* VES002 (as deposited with the BCCM/LMG under the accession number LMG P-28149 on Jan. 27, 2014).

Statement 11. The composition for use according to statement 8, or 10, use according to any one of statements 5, 6 or 9, or 10, or the method according to statement 7, or 10, wherein the immunity improvement comprises:

- an increase of the number of antigen presenting cells (APCs), preferably type 1 conventional dendritic cells (cDC1) and/or plasmacytoid dendritic cells (pDCs), in the lungs of the subject or the offspring;
- an increase of the number of antigen presenting cells (APCs), preferably type 1 conventional dendritic cells (cDC1) and/or plasmacytoid dendritic cells (pDCs), in lymph nodes, preferably lung-draining lymph nodes, more preferably mediastinal lymph nodes, of the subject or the offspring upon a viral respiratory infection;
- an increase of the number of IFNγ-producing CD8+ T cells in the lungs of the subject or the offspring upon a viral respiratory infection;
- an increased synthesis of pro-inflammatory cytokines and/or chemokines, preferably one or more such as all of Ifnγ, CXCL9 and CXCL10, in the lungs of the subject or the offspring upon a viral respiratory infection;
- an increased synthesis of Eomes transcription factor in the lungs of the subject or the offspring upon a viral respiratory infection;
- an increase of the number of virtual memory (VM) CD8+ T cells, in particular IFN-γ producing and/or TNF-α producing CXCR3+ VM CD8+ T cells, in the lungs of the subject or the offspring upon a viral respiratory infection;
- an increase of the number of innate immune cells, preferably alveolar macrophages and/or natural killer cells, in the lungs of the subject or the offspring upon a viral respiratory infection;
- an increase of the number of TNF-α producing innate immune cells, preferably TNF-α producing alveolar macrophages, natural killer cells and/or neutrophils, in the lungs of the subject or the offspring upon a viral respiratory infection; or
- any combination thereof.

Statement 12. A composition comprising an effective amount of a probiotic for use in the prevention or treatment of a viral respiratory infection in a subject, wherein said composition is administered to the subject's pregnant or lactating mother, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain, preferably wherein said probiotic consists of a *Lactobacillus rhamnosus* strain, or a *Lactobacillus johnsonii* strain, or a *Bifidobacterium animalis* spp *lactis* strain, or a *Lactobacillus rhamnosus* strain and a *Bifidobacterium animalis* spp *lactis* strain.

Statement 13. Use of a probiotic in the manufacturing of a composition, preferably a food nutritional composition, for administration to a pregnant or lactating mother for the prevention or treatment of a viral respiratory infection in the offspring, wherein said probiotic comprises or consists of a

*Lactobacillus* strain, preferably a *Lactobacillus rhamnosus* strain and/or a *Lactobacillus johnsonii* strain, and/or a *Bifidobacterium animalis* spp *lactis* strain preferably wherein said probiotic consists of a *Lactobacillus rhamnosus* strain or a *Lactobacillus johnsonii* strain or a *Bifidobacterium animalis* spp *lactis* strain, or a *Lactobacillus rhamnosus* strain and a *Bifidobacterium animalis* spp *lactis* strain.

Statement 14. A method for the prevention or treatment of a viral respiratory infection in a subject, said method comprising the administration of a composition comprising an effective amount of a probiotic to the subject's pregnant or lactating mother, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain, preferably wherein said probiotic consists of a *Lactobacillus rhamnosus* strain or a *Lactobacillus johnsonii* strain or a *Bifidobacterium animalis* spp *lactis* strain, or a *Lactobacillus rhamnosus* strain and a *Bifidobacterium animalis* spp *lactis* strain.

Statement 15. Use of a probiotic in the manufacturing of a medicament or pharmaceutical composition for administration to a pregnant or lactating mother for the prevention or treatment of a viral respiratory infection in the offspring, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain, preferably wherein said probiotic consists of a *Lactobacillus rhamnosus* strain or a *Lactobacillus johnsonii* strain or a *Bifidobacterium animalis* spp *lactis* strain, or a *Lactobacillus rhamnosus* strain and a *Bifidobacterium animalis* spp *lactis* strain.

Statement 16. The composition for use according to statement 8, 10 or 11 or 12, use according to any one of statements 5, 6, 9, 10 or 11 or 13 or 15, or the method according to statement 7, 10 or 11, or 14, wherein the composition is not administered to the subject/offspring.

Statement 17. The composition for use according to statement 8, 10 or 11, or 12, or 16 use according to any one of statements 5, 6, 9, 10 or 11, or 13 or 15, or 16, or the method according to statement 7, 10 or 11, or 14, or 16, wherein the subject/offspring is less than about 18 years old, preferably less than about 12 years old, more preferably less than about 6 years old.

Statement 18. The composition for use according to any one of statements 8, 10 or 11, or 12, or 16 or 17, use according to any one of statements 5, 6, 9, 10 or 11, or 13 or 15, or 16 or 17, or the method according to any one of statements 7, 10 or 11, or 14, or 16 or 17, wherein the subject/offspring is less than 2 years old, preferably less than 1 year old.

Statement 19. The composition for use according to any one of statements 8, 10 or 11, or 12, or 16 to 18, use according to any one of statements 5, 6, 9, 10 or 11, or 13 or 15, or 16 to 18, or the method according to any one of statements 7, 10 or 11, or 14, or 16 to 18, wherein the subject/offspring is a neonate (from 0 days to about 28 days).

Statement 20. The composition for use according to any one of statements 12, or 16 to 19, use according to any one of statements 13 or 15, or 16 to 19, or the method according to any one of statements 14, or 16 to 19, wherein the viral respiratory infection is selected from an influenza virus infection, a rhinovirus infection, a respiratory syncytial virus infection, a parainfluenza virus infection, a coronavirus infection or an adenovirus infection.

Statement 21. The composition for use according to any one of statements 12, or 16 to 20, use according to any one of statements 13 or 15, or 16 to 20, or the method according to any one of statements 14, or 16 to 20, wherein the viral respiratory infection is an influenza virus infection, preferably an influenza A virus infection, more preferably an influenza A H1N1 virus infection.

Statement 22. The composition for use according to any one of statements 12, or 16 to 21, use according to any one of statements 2 to 4, 13 or 15, or 16 to 21, or the method according to any one of statements 14, or 16 to 21, wherein the *Lactobacillus rhamnosus* strain is *Lactobacillus rhamnosus* VES001.

Statement 23. The composition for use according to any one of statements 12, or 16 to 22, use according to any one of statements 2 to 4, 13 or 15, or 16 to 22, or the method according to any one of statements 14, or 16 to 22, wherein the *Bifidobacterium animalis* spp *lactis* strain is *Bifidobacterium animalis* spp *lactis* VES002 (as deposited with the BCCM/LMG under the accession number LMG P-28149 on Jan. 27, 2014).

Statement 24. The composition for use according to any one of statements 8, 10 or 11, or 12, or 16 to 23, use according to any one of statements 3 or 4, 5, 6, 9, 10 or 11, or 13 or 15, or 16 to 23, or the method according to any one of statements 7, 10 or 11 or 14, or 16 to 23, wherein the composition is administered orally to the pregnant or lactating mother.

Statement 25. The composition according to statement 1, the composition for use according to any one of statements 8, 10 or 11, or 12, or 16 to 24, use according to any one of statements 3 or 4, 5, 6, 10 or 11, or 13, or 16 to 24, or the method according to any one of statements 7, 10 or 11, or 14, or 16 to 24, wherein the composition is a (maternal) nutritional composition, preferably a composition selected from a food product, a food ingredient, or a (maternal) food supplement.

Statement 26. The composition according to statement 1 or 25, the composition for use according to any one of statements 8, 10 or 11, or 12, or 16 to 25, use according to any one of statements 3 or 4, 5, 6, 9, 10 or 11, or 13 or 15, or 16 to 25, or the method according to any one of statements 7, 10 or 11, or 14, or 16 to 25, wherein the composition is in a solid dosage form, such as in the form of a tablet, a capsule, an orosoluble capsule, a sachet, a powder, a chewing gum, a softgel capsule; or in a liquid dosage form, such as in the form of a suspension.

Statement 27. The composition according to any one of statements 1, or 25 or 5, 26, the composition for use according to any one of statements 8, 10 or 11, or 12, or 16 to 26, use according to any one of statements 3 or 4, 5, 6, 9, 10 or 11, or 13 or 15, or 16 to 26, or the method according to any one of statements 7, 10 or 11, or 14, or 16 to 26, wherein the composition comprises the probiotic in an amount of between $1\times10^4$ cfu and $1\times10^{12}$ cfu, preferably between $1\times10^7$ cfu and $1\times10^{12}$ cfu, more preferably between $1\times10^7$ cfu and $1\times10^{11}$ cfu, per dose.

Statement 28. The composition according to any one of statements 1, or 25 to 27, the composition for use according to any one of statements 8, 10 or 11, or 12, or 16 to 27, use according to any one of statements 3 or 4, 5, 6, 9, 10 or 11, or 13 or 15, or 16 to 27, or the method according to any one of statements 7, 10 or 11, or 14, or 16 to 27, wherein the composition further comprises one or more, such as all, of a vitamin and a mineral.

Statement 29. The composition according to any one of statements 1, or 25 to 28, the composition for use according to any one of statements 8, 10 or 11 or 12, or 16 to 28, use according to any one of statements 3 or 4, 5, 6, 9, 10 or 11, or 13 or 15, or 16 to 28, or the method according to any one of statements 7, 10 or 11, or 14, or 16 to 28, wherein the composition further comprises a prebiotic.

Statement 30. The composition according to any one of statements 1, or 25 to 29, the composition for use according to any one of statements 8, 10 or 11, or 12, or 16 to 29, use according to any one of statements 3 or 4, 5, 6, 9, 10 or 11, or 13 or 15, or 16 to 29, or the method according to any one of statements 7, 10 or 11, or 14, or 16 to 29, wherein the composition further comprises an omega-3 fatty acid source.

Statement 31. The composition for use according to any one of statements 8, 10 or 11, or 12, or 16 to 30, use according to any one of statements 3 or 4, 5, 6, 9, 10 or 11, or 13 or 15, or 16 to 30, or the method according to any one of statements 7, 10 or 11, or 14, or 16 to 30, wherein the composition is administered daily to the pregnant or lactating mother, preferably in one dose given daily.

Statement 32. The composition for use according to any one of statements 8, 10 or 11, or 12, or 16 to 31, use according to any one of statements 3 or 4, 5, 6, 9, 10 or 11, or 13 or 15, or 16 to 31, or the method according to any one of statements 7, 10 or 11, or 14, or 16 to 31, wherein the composition is administered to the pregnant mother for at least 4 weeks before delivery, preferably for at least 2 months before delivery, more preferably at least during the third trimester of pregnancy or at least during the second and third trimester of pregnancy.

Statement 33. The composition for use according to any one of statements 8, 10 or 11, or 12, or 16 to 32, use according to any one of statements 3 or 4, 5, 6, 9, 10 or 11, or 13 or 15, or 16 to 32, or the method according to any one of statements 7, 10 or 11, or 14, or 16 to 32, wherein the composition is administered to the lactating mother for at least 1 week after delivery, preferably for at least 1 or 2 months after delivery, more preferably for at least 3 to 6 months after delivery.

Statement 34. The composition for use according to any one of statements 8, 10 or 11, or 12, or 16 to 33, use according to any one of statements 3 or 4, 5, 6, 9, 10 or 11, or 13 or 15, or 16 to 33, or the method according to any one of statements 7, 10 or 11, or 14, or 16 to 33, wherein the composition is administered to the mother at least during the third trimester of pregnancy and for at least 1 or 2 months after delivery when the mother is breastfeeding.

Statement 35. The composition for use according to any one of statements 8, 10 or 11, or 12, or 16 to 34, use according to any one of statements 3 or 4, 5, 6, 9, 10 or 11, or 13 or 15, or 16 to 34, or the method according to any one of statements 7, 10 or 11, or 14, or 16 to 34, wherein the composition is administered to the mother at least during the third trimester of pregnancy and for at least 3 to 6 months after delivery when the mother is breastfeeding.

Statement 36. The composition for use according to any one of statements 8, 10 or 11, or 12, or 16 to 35, use according to any one of statements 5, 6, 9, 10 or 11, or 13 or 15, or 16 to 35, or the method according to any one of statements 7, 10 or 11, or 14, or 162 to 35, wherein the mother and the subject/offspring is a human.

Those skilled in the art will recognize the many other effects and advantages of the present methods, uses or products, and the numerous possibilities for end uses of the present invention from the detailed description and examples provided below.

DETAILED DESCRIPTION OF THE INVENTION

Figure 1:
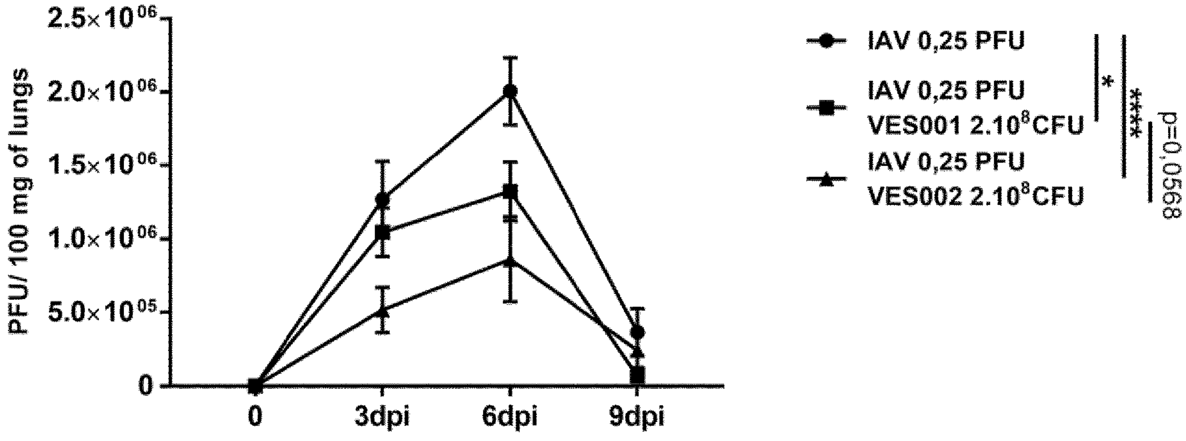
FIG. 1. Impact of maternal supplementation with *L. rhamnosus* VES001 or *B. lactis* VES002 during the gestation and lactation period on viral load (expressed as PFU/100 mg of lungs) in neonatal lungs. Viral load was measured in lungs of 3-days-old uninfected neonates (0) (n=7) and of neonates infected with influenza A from mothers not supplemented with probiotics (IAV 0.25 PFU) or supplemented with VES001 (IAV 0.25 PFU; VES001 $2 \cdot 10^8$) or VES002 (IAV 0.25 PFU; VES001 $2 \cdot 10^8$) at 3, 6 or 9 days post-infection (3 dpi, 6 dpi, 9 dpi). 3 dpi IAV: n=10; 3 dpi IAV VES001: n=15; 3 dpi IAV VES002: n=10: 6 dpi IAV: n=9; 6 dpi IAV VES001: n=9; 6 dpi IAV VES002: n=7; 9 dpi IAV: n=5; 9 dpi IAV VES001: n=9; 9 dpi IAV VES002: n=6. Statistical significance was determined by a Two-way ANOVA (parametrics). *p<0.05 ****p<0.005.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of ±10% or less, preferably ±5% or less, more preferably ±1% or less, and still more preferably ±0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

As corroborated by the experimental section, which illustrates certain representative embodiments of the invention, the inventors realized that probiotic intervention during pregnancy and optionally the lactation period protects the progeny from viral infections of the respiratory tract. In particular, the present inventors found reduced viral loads in the respiratory tract of progeny infected with an influenza virus H1N1 strain from mothers that were administered a probiotic, in particular *Lactobacillus rhamnosus* or *Bifidobacterium animalis* spp *lactis*, during pregnancy and lactation relative to progeny of mothers not treated with the probiotic who were exposed to the same viral threat.

Accordingly, an aspect relates to a composition comprising a probiotic for use in the prevention or treatment of a viral respiratory infection in a subject, wherein said composition is administered to the subject's pregnant or lactating mother, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain.

A related aspect is directed to a method for the prevention or treatment of a viral respiratory infection in a subject, said method comprising the administration of a composition comprising a probiotic to the subject's pregnant or lactating mother, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain.

A related aspect is directed to use of a probiotic in the manufacturing of a medicament for administration to a pregnant or lactating mother for the prevention or treatment of a viral respiratory infection in the offspring, wherein said probiotic comprises or consists of a *Lactobacillus* strain, preferably a a *Lactobacillus rhamnosus* strain and/or a *Lactobacillus johnsonii* strain, and/or a *Bifidobacterium animalis* spp *lactis* strain.

A related aspect is directed to use of a probiotic in the manufacturing of a composition, preferably a nutritional composition, for administration to a pregnant or lactating mother for the prevention or treatment of a viral respiratory infection in the offspring, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain.

The terms "respiratory infection" or "respiratory tract infection" generally refer to a disease or disorder affecting at least a part of the respiratory tract (i.e. respiratory system). In particular, a respiratory infection may affect, without limitation, the nose, sinuses, throat, pharynx, larynx, airways, lungs, or any combination thereof. An "upper respiratory infection" refers to a respiratory infection affecting the upper respiratory tract, including the nose, sinuses, pharynx, larynx, or any combination thereof. Non-limiting examples of upper respiratory infections include tonsillitis, pharyngitis (sore throat), rhinitis, rhinosinusitis, nasopharyngitis, laryngitis, sinusitis (sinus infection), laryngopharyngitis, larynepiglottis, laryngotracheitis, tracheitis, otitis media, and a common cold. A "lower respiratory infection" "refers to a respiratory infection affecting the lower respiratory tract, including bronchi, bronchioles, alveoli, pleura, pleural cavity, or any combination thereof. In general, lower respiratory infections last longer and are more serious compared to upper respiratory infection. Non-limiting examples of lower respiratory infections include bronchitis (infection of the bronchial tubes), bronchiolitis (infection of the bronchioles), chest infection and pneumonia (infection of the alveoli). In the context of the present invention, both symptomatic and asymptomatic respiratory infections are envisaged. It is understood that the term "symptomatic" indicates the presence of one or more physical representations (i.e. symptoms) of the respiratory infection. Typical symptoms of a respiratory infection are diverse and may include, without limitation, coughing (phlegm), sneezing, congestion of the nasal sinuses and/or lungs, runny nose, throat pain and/or irritation, muscle ache, shortness of breath, wheezing, tight chest tightness, fever, malaise, itchy and/or watery eyes, and any combination thereof.

Respiratory infections can be caused by viruses or bacteria entering the respiratory system. As used herein, a "viral respiratory infection" refers to a respiratory infection caused by a virus. Over 200 different viruses can cause respiratory infections, including, for example, rhinovirus, coronavirus, parainfluenza virus, adenovirus, enterovirus, respiratory syncytial virus (RSV), bocavirus, influenza viruses, human metapneumovirus (hMPV), orthomyxoviridae, cytomegalovirus, Epstein-Barr virus, herpes simplex virus, and morbilli virus.

Influenza viruses are classified into types A, B, C, etc. Type A and type B are common, and influenza A virus is the most prevailing type. Influenza A virus is a single-stranded negative-sense RNA virus having an envelope, which belongs to the family Orthomyxoviridae. Its subtypes are determined by 16 kinds of hemagglutinin (H1 to H16) and 9 kinds of neuraminidase (N1 to N9), which are surface antigens.

In certain embodiments, the viral respiratory infection is selected from an influenza virus infection, a rhinovirus infection, a respiratory syncytial virus infection, a parainfluenza virus infection, a coronavirus infection or an adenovirus infection.

In particular embodiments, the viral respiratory infection is an influenza virus infection, in particular an influenza A virus infection, more particularly an influenza A H1N1 virus infection.

The terms "treatment" or "treat" as used herein generally refers to the alleviation or measurable lessening of one or more symptoms or measurable markers of a pathological condition such as a disease or disorder, in particular a viral respiratory infection. Measurable lessening includes any statistically significant decline in a measurable marker or symptom. The terms encompass primary treatments as well as neo-adjuvant treatments, adjuvant treatments and adjunctive therapies. The term encompass both the therapeutic treatment of an already developed pathological condition, as well as prophylactic or preventative measures, wherein the aim is to prevent or reduce the chances of incidence of a pathological condition such as a disease or disorder, in particular a viral respiratory infection. An effective treatment in the context of a viral respiratory infection as taught herein can include e.g. a reduction in one or more symptoms of the viral respiratory infection such as a reduction in viral load, a reduced need for respiratory assistance (e.g., ventilator, supplementary oxygen, etc.), reduced hospital stay, reduced duration of the respiratory viral infection, reduced absence (i.e., fewer days absent), reduced likelihood of developing complications, etc.

The use of a composition comprising the probiotic as taught herein may be very beneficial in the sense of being usable prophylactically, i.e. before a viral respiratory infection has developed. The terms "prevention" or "prevent" as used in the context of the invention are defined as ameliorating the risk of suffering from a viral respiratory infection and refers to treatments wherein the object is to avoid or to reduce the risk of a subject's body or an element thereof to show clinical symptoms of a viral respiratory infection, and/or to reduce the severity, the duration and/or the symptoms of a viral respiratory infection as compared to a subject not being treated according to the invention.

Without wishing to be bound by any theory, the probiotic may exercise its beneficial effect on the prevention or treatment of a viral respiratory infection in the subject via improving immunity of the subject. Accordingly, in a further aspect, the present invention also relates to a composition comprising a probiotic as taught herein for use in improving immunity in a subject, wherein said composition is administered to the subject's pregnant or lactating mother, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain.

A related aspect is directed to a method for improving immunity in a subject, said method comprising the administration of a composition comprising a probiotic as taught herein to the subject's pregnant or lactating mother, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain.

A related aspect is directed to use of a probiotic in the manufacturing of a medicament for administration to a pregnant or lactating mother for improving immunity in the offspring, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain.

A related aspect is directed to use of a probiotic in the manufacturing of a composition, preferably a nutritional composition, for administration to a pregnant or lactating mother for improving immunity in the offspring, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain.

A related aspect is directed to non-therapeutic use of a composition comprising a probiotic as taught herein for use in improving immunity in a subject, wherein said composition is administered to the subject's pregnant or lactating mother, wherein said probiotic comprises or consists of a *Lactobacillus* strain, preferably a *Lactobacillus rhamnosus* strain and/or a *Lactobacillus johnsonii* strain, and/or a *Bifidobacterium animalis* spp *lactis* strain.

In certain embodiments, the immunity improvement comprises an increase of the number of antigen presenting cells (APCs), preferably type 1 conventional dendritic cells (cDC1) and/or plasmacytoid dendritic cells (pDCs), in the lungs of the subject or the offspring, in particular wherein said increase is relative to the number of APCs in the lungs of a subject or offspring whose pregnant or lactating mother was not administered the probiotic.

In certain embodiments, the immunity improvement comprises an increase of the number of antigen presenting cells (APCs), preferably type 1 conventional dendritic cells (cDC1) and/or plasmacytoid dendritic cells (pDCs), in lymph nodes, preferably lung-draining lymph nodes, more preferably mediastinal lymph nodes, of the subject or the offspring upon a viral respiratory infection (or the infected subject or the infected offspring), in particular wherein said increase is relative to the number of APCs in lymph nodes of an infected subject or offspring whose pregnant or lactating mother was not administered the probiotic.

As used herein, "type 1 conventional dendritic cells" or "cDCs 1" refer to a subset of conventional dendritic cells. They are major stimulators of T cells.

As used herein, "plasmacytoid dendritic cells" or "pDCs" refer to a division of dendritic cells characterized in that they can produce high amounts of antiviral type I interferon during an infection.

In certain embodiments, the immunity improvement comprises an increase of the number of IFNγ-producing CD8+ T cells in the lungs of the subject or the offspring upon a viral respiratory infection, in particular wherein said increase is relative to the number of IFNγ-producing CD8+ T cells of an infected subject or offspring whose pregnant or lactating mother was not administered the probiotic.

In certain embodiments, the immunity improvement comprises an increased synthesis of pro-inflammatory cytokines and/or chemokines, preferably one or more such as all of Ifnγ, CXCL9 and CXCL10, in the lungs of the subject or the offspring upon a viral respiratory infection, in particular wherein said increase is relative to the synthesis of pro-inflammatory cytokines and/or chemokines in the lungs of an infected subject or offspring whose pregnant or lactating mother was not administered the probiotic.

In certain embodiments, the immunity improvement comprises an increased synthesis of Eomes transcription factor in the lungs of the subject or the offspring upon a viral respiratory infection, in particular wherein said increase is relative to the synthesis of Eomes transcription factor in the lungs of an infected subject or offspring whose pregnant or lactating mother was not administered the probiotic.

In certain embodiments, the immunity improvement comprises an increase of the number of virtual memory (VM) CD8+ T cells, in particular IFN-γ producing and/or TNF-α producing CXCR3+ VM CD8+ T cells, in the lungs of the subject or the offspring upon a viral respiratory infection, in particular wherein said increase is relative to the number of VM CD8+ T cells in the lungs of an infected subject or offspring whose pregnant or lactating mother was not administered the probiotic.

As used herein, "virtual memory CD8+ T cells" or "VM CD8+ T cells" or "virtual memory cells" or "virtual memory T cells" refer to a subtype of T lymphocytes, in particular a CD8+ T cell type that exhibits a memory phenotype without having been exposed to a foreign antigen. VM cells exhibit protective effector functions such as the synthesis of IFN-γ and TNF-α. They are further characterized by expression of the transcription factor Eomes and the chemokine receptor CXCR3.

In certain embodiments, the immunity improvement comprises an increase of the number of innate immune cells, preferably alveolar macrophages and/or natural killer cells, in the lungs of the subject or the offspring upon a viral respiratory infection, in particular wherein said increase is relative to the number of innate immune cells in the lungs of an infected subject or offspring whose pregnant or lactating mother was not administered the probiotic.

In certain embodiments, the immunity improvement comprises an increase of the number of TNF-α producing innate immune cells, preferably TNF-α producing alveolar macrophages, natural killer cells and/or neutrophils, in the lungs of the subject or the offspring upon a viral respiratory infection, in particular wherein said increase is relative to the number of TNF-α producing innate immune cells in the lungs of an infected subject or offspring whose pregnant or lactating mother was not administered the probiotic.

The term "subject" as used throughout this specification typically and preferably denotes a human, but may also encompass reference to non-human animals, preferably warm-blooded animals, even more preferably mammals, such as, e.g., non-human primates, rodents, canines, felines, equines, ovines, porcines, and the like. The term "non-human animals" includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. For example, the subject may be a non-human mammal. In preferred embodiments of the methods or uses as taught herein, the subject is a human subject The term does not denote a particular sex or age. Thus, with limitation, adult subjects, elderly subjects, teenagers, children and infants, both males and females, are intended to be covered by the term "subject".

In particular embodiments of the methods or uses as taught herein, the subject is a pediatric subject or a teenager, preferably a pediatric subject. As used herein, a "pediatric subject" denotes a human no greater than 13 years of age and may refer to newborns, infants and/or children. A "newborn" or "neonate" as used herein refers to a subject, in particular a human, from birth to about 4 weeks or 28 days of age. An "infant" generally refers to a subject, in particular a human, from birth to about 12 months of age. In embodiments, an infant refers to a subject, in particular a human, between about 1 month and about 12 months of age. A "child" means a subject, in particular a human, ranging in age from about 12 months to 13 years and may refer to any range of ages between about 12 months and 13 years. For example, a child may refer to a subject, in particular a human, that is between about 12 months and about 6 years in age, or between about 12 months and about 2 years of age, or between about 2 years and about 12 years of age, or between about 2 years and about 6, 7 or 8 years of age, or between about 6, 7 or 8 years and about 12 years of age. A "teenager" refers to a subject, in particular a human, of the age of 13 to 19 years.

In particular embodiments, the subject may be from 0 days to about 18 years old, preferably from 0 days to about 13 years old, such as from 0 days to about 12, 11, 10, 9, 8 or 7 years old, more preferably from 0 days to about 6 years old such as from 0 days to about 5, 4 or 3 years old, even more preferably from 0 days to about 2 years old. In particular embodiments, the subject may be from 0 days to about 1 year old. In particular embodiments, the subject may be from 0 days to 28 days old (i.e. a neonate).

The subject may also be a fetus (prenatal treatment). In particular embodiments, the subject may be under the age of about 18 years old, preferably under the age of about 13 years old, such as under the age of about 12, 11, 10, 9, 8 or 7 years old, more preferably under the age of about 6 years old such as under the age of about 5, 4 or 3 years old, even more preferably under the age of about 2 years old. In particular embodiments, the subject may be under the age of about 1 year old. In particular embodiments, the subject may be under the age of 28 days old (i.e. a fetus or a neonate).

According to the invention, a composition comprising a probiotic is administered to the subject's pregnant mother and/or, preferably and, also the same mother after delivery, while lactating, to prevent or treat the subject (i.e. the offspring) of a viral respiratory infection. Suitable subjects that would benefit from a treatment as taught herein include, without limitation, subjects being at risk for developing a viral respiratory infection such as, for example, infants and young children in a day care centre, premature infants and young children, infants and young children who are not breast fed.

In particular embodiments, the composition comprising the probiotic is not administered to the subject/offspring.

The term "probiotic" generally refers to microorganisms, microbial cell preparations or components of microbial cells (e.g., cell wall constituents (e.g., peptidoglycans, proteins, polysaccharides, teichoic acid, etc.), cell organelles, nucleic acids, cell membrane constituents and cell metabolites (e.g., organic acids, inorganic acids, proteins, peptides, amino acids, enzymes, lipids, carbohydrates, glycolipids, glycoproteins, vitamins, salts, metals, etc.)), with a beneficial effect on the health or well-being of the host. In embodiments, the probiotic in the composition as taught herein is a viable microorganism or bacterium. The term "viable" as used herein in connection with a microorganism or bacterium denotes a microorganism or bacterium that is metabolically active. Probiotic microorganisms generally have the ability to survive the passage through the upper part of the digestive tract. They are preferably non-pathogenic and non-toxic. Without wishing to be bound by any theory, probiotic microorganisms are believed to exercise their beneficial effect on health on the one hand via ecological interactions with the resident flora in the digestive tract, and on the other hand via their ability to influence the immune system in a positive manner via the "GALT" (gut-associated lymphoid tissue). The probiotic used in the methods, uses and compositions as taught can comprise a unique strain of a microorganism, a mix of various strains and/or a mix of various bacterial species and genera.

The probiotic used in the methods, uses and compositions as taught herein may be selected from a *Lactobacillus* strain, preferably a *Lactobacillus rhamnosus* strain or a *Lactobacillus johnsonii* strain, more preferably a *Lactobacillus rhamnosus* strain; a Bifodobacterium strain, preferably a *Bifidobacterium animalis* strain, more preferably a *Bifidobacterium animalis* spp *lactis* strain; or any combination thereof. In particular embodiments, the probiotic consists of a *Lactobacillus rhamnosus* strain and/or a *Bifidobacterium animalis* spp *lactis* strain.

As used herein "*Lactobacillus rhamnosus*" or "*Lacticaseibacillus rhamnosus*" or "*L. rhamnosus*" refers to a bacterium that originally was considered to be a subspecies of *L. casei*, but genetic research found it to be a separate species in the *L. casei* clade. It is a short Gram-positive homofermentative facultative anaerobic non-spore-forming rod that often appears in chains. Non-limiting examples of suitable strains of *Lactobacillus rhamnosus* include *L. rhamnosus* VES01 and *Lactobacillus rhamnosus* GG (*Lactobacillus* GG., ATCC number 53103).

In particularly preferred embodiments, the probiotic comprises or consists of *L. rhamnosus* VES001 (or LMG S-28148), which was deposited with the BCCM (Belgian Coordinated Collections of Micro-organisms)—LMG (Laboratorium voor Microbiologie—Bacteriënverzameling) (BCCM/LMG), Universiteit Gent, K. L. Ledeganckstraat 35, 9000 Ghent, Belgium on Jan. 27, 2014 according to the Treaty of Budapest.

Bifidobacteria are gram-positive anaerobes that operate in the lower part of the digestive system. They are non-motile, non-spore forming and catalase-negative. They have various shapes, including short, curved rods, club-shaped rods and bifurcated Y-shaped rods. They are classified as lactic acid bacteria due to their production of lactic acid during carbohydrate fermentation. *Bifidobacterium animalis* is a rod-shaped bacterium of the *Bifidobacterium* genus which can be found in the large intestines of most mammals, including humans. *Bifidobacterium animalis* and *Bifidobacterium lactis* were previously described as two distinct species. Presently, both are considered *B. animalis* with the subspecies *Bifidobacterium animalis* subsp. *animalis* and *Bifidobacterium animalis* subsp. *lactis*. Non-limiting examples of suitable strains of Bifidobacteria that are useful in the present invention are *Bifidobacterium animalis* spp *lactis* VES002 and *Bifidobacterium animalis* subsp. *lactis* BB-12® (as available from Chr. Hansen Biosystems).

In particularly preferred embodiments, the probiotic comprises or consists of *Bifidobacterium animalis* spp *lactis* VES002, which was deposited with the BCCM (Belgian Coordinated Collections of Micro-organisms)—LMG (Laboratorium voor Microbiologie—Bacteriënverzameling) (BCCM/LMG), Universiteit Gent, K. L. Ledeganckstraat 35, 9000 Ghent, Belgium on Jan. 27, 2014 according to the Treaty of Budapest, under the number of LMG P-28149.

According to the invention, a composition comprising a probiotic is administered to the subject's pregnant or expectant mother and/or, preferably and, also the same mother after delivery, while lactating. In particular, a composition comprising a probiotic as taught herein is administered to a pregnant or expecting mother and/or, preferably and, also to the same mother after delivery, while lactating, to prevent or treat the offspring of a viral respiratory infection.

Thus, the subject's mother receives the probiotic during at least part or all of her pregnancy and/or, preferably and, after delivery, during at least part or all of the lactation period if she is lactating or breastfeeding. According to a preferred embodiment, the composition comprising the probiotic is administered to the pregnant mother (also referred to herein as expecting mother) and to the same mother while lactating (also referred to herein as lactating or breastfeeding mother).

The administration period to the pregnant mother may cover substantially the full length of the pregnancy or gestation period, or may be less. In a particular embodiment, the composition comprising the probiotic is administered during the full duration of the pregnancy. The pregnant mother may start to take the composition comprising the probiotic as soon as she is aware of her pregnancy. The administration period may also start before pregnancy starts, for example if the female is trying to become pregnant. Administration may also start at any time after the pregnancy starts. In embodiments, the composition comprising the probiotic is administered to the subject's pregnant mother for at least two weeks before delivery, preferably for at least four weeks before delivery, more preferably during at least the last 2 months of pregnancy, even more preferably for at least 3, 4, 5 or more months before delivery. In certain embodiments, the composition comprising the probiotic is administered at least during the third trimester of the pregnancy such as during the third trimester of the pregnancy or at least during the second and third trimesters of the pregnancy such as during the second and third trimesters of the pregnancy.

The administration period to the subject's lactating mother preferably covers substantially the full length of the lactation period, or may be less. In particular embodiments, the composition comprising the probiotic is administered during the full duration of lactation. In embodiments, the composition comprising the probiotic as taught herein is administered to the subject's lactating mother, for at least 1 or 2 weeks after delivery, preferably for at least 1 month or 2 months after delivery, more preferably for at least 3 months after delivery such as for at least 4, 5 or 6 months after delivery or for at least 3 to 6 months after deliveryor for at least 7, 8, 9, 10, 11 or 12 months after delivery.

In particular embodiments, the composition comprising the probiotic is administered to the subject's mother for at least 4 weeks before delivery and for at least 1 or 2 months after delivery when the mother is breastfeeding. In particular embodiments, the composition comprising the probiotic is administered to the subject's mother for at least 4 weeks before delivery and for at least 3 to 6 months after delivery when the mother is breastfeeding. In particular embodiments, the composition comprising the probiotic is administered to the subject's mother at least during the third trimester of the pregnancy and for at least 1 or 2 months after delivery when the mother is breastfeeding. In particular embodiments, the composition comprising the probiotic is administered to the subject's mother at least during the third trimester of the pregnancy and for at least 3 to 6 months after delivery when the mother is breastfeeding. In particular embodiments, the composition comprising the probiotic is administered to the subject's mother at least during the second and third trimesters of the pregnancy and for at least 1 or 2 months after delivery when the mother is breastfeeding. In particular embodiments, the composition comprising the probiotic is administered to the subject's mother at least during the second and third trimesters of the pregnancy and for at least 3 to 6 months after delivery when the mother is breastfeeding.

The probiotic can be administered to the pregnant or lactating mother by various ways. For example, the composition can be provided for use and intake orally, or sublingually, but also respiratory, preferably nasal or bronchial, or even rectally. The composition can also be an injectable liquid composition, e.g. for subcutaneous injection.

In certain embodiments, the probiotic is orally administered to the pregnant or lactating mothers e.g. as part of the food, as a drink or as a dietary supplement. The probiotic can also be orally administered in a pharmaceutical composition.

A skilled person is aware that in order to achieve an effective prevention or treatment of a viral respiratory infection in the subject (or the progeny), an effective dose of the probiotic needs to be administered to the pregnant or lactating mother. In the context of the present disclosure "an effective amount" or "an effect dose" refers to an amount or quantity of the probiotic necessary to obtain a physiological effect. The physiological effect may be achieved by a single dose or by multiple doses. A "therapeutically effective amount" or "therapeutically effective dose" indicates an amount of probiotic that when administered to the pregnant or lactating mother brings about a clinical positive response with respect to therapeutic treatment of the subject or the progeny afflicted by a viral respiratory infection. Similarly, a "prophylactically effective amount" or "prophylactically effective dose" refers to an amount of probiotic that inhibits or delays the onset of a viral respiratory infection and/or prevents or reduces the risk of a clinical manifestation of a viral respiratory infection and/or reduces the severity, symptoms and/or duration of a viral respiratory infection in the subject or the progeny. A skilled person is aware that terms such as "quantity", "amount" and "level" are synonyms and have a well-defined meaning in the art and appreciates that these may particularly refer to an absolute quantification of a probiotic which is considered an effective amount for the applications described herein, or to a relative quantification of the probiotic, such as for example a concentration of probiotic in function of e.g. the bodyweight of the pregnant or lactating mother.

Thus, the probiotic may be present in the composition as taught herein in a wide range of percentages provided that it delivers an effective prevention or treatment of a viral respiratory infection in the subject or the progeny. It is well within the level of knowledge of one of skill in the art to determine an effective dosage of an active compound or ingredient such as a probiotic. The size and frequency of the dosage may depend, for example, upon the probiotic microorganism chosen, the delivery vehicle, the mode of administration, interference or influence by or efficacy of other active ingredients in the composition, etc.

Preferable doses, in particular daily doses, of each of the probiotic as taught herein for administration to the subject's pregnant or lactating mother may be from $1\times10^4$ to $1\times10^{12}$ cfu, such as from $1\times10^5$ to $1\times10^{12}$ cfu, from $1\times10^6$ to $1\times10^{12}$ cfu, or from $1\times10^7$ to $1\times10^{12}$ cfu, preferably from $1\times10^7$ to $1\times10^{11}$ cfu, such as from $1\times10^8$ to $1\times10^{11}$ cfu, or from $1\times10^7$ to $5\times10^{10}$ cfu, more preferably from $1\times10^8$ to $5\times10^{10}$ cfu such as from $1\times10^8$ to $1\times10^{10}$ cfu (cfu=colony forming unit).

The probiotic may be present in a composition in an amount equivalent to between $1\times10^2$ and $1\times10^{12}$ cfu/g of dry composition, such as between $1\times10^3$ and $1\times10^{12}$ cfu/g of dry composition, preferably between $1\times10^4$ and $1\times10^{12}$ cfu/g of dry composition, such as between $1\times10^5$ and $1\times10^{12}$, between $1\times10^6$ and $1\times10^{12}$, or between $1\times10^7$ and $1\times10^{12}$ cfu/g of dry composition; more preferably between $1\times10^7$ and $1\times10^{11}$ cfu/g of dry composition, such as between $1\times10^8$ and $1\times10^{11}$, or between $1\times10^7$ and $5\times10^{10}$ cfu/g of dry composition; even more preferably between $1\times10^8$ and $5\times10^{10}$ cfu/g of dry composition such as between $1\times10^8$ to $1\times10^{10}$ cfu/g of dry composition. This includes the possibilities that the bacteria are live, inactivated or dead or even present as fragments such as DNA or cell wall materials. In other words, the quantity of bacteria which the formula contains is expressed in terms of the colony forming ability of that quantity of bacteria as if all the bacteria were live irrespective of whether they are, in fact, live, inactivated or dead, fragmented or a mixture of any or all of these states.

The administration of the composition comprising the probiotic as taught herein to the mother may be, for example, by daily intake (e.g. to be taken once or twice a day), every second day, or weekly intake (e.g. to be taken one or twice a week). In preferred embodiments, the composition is administered daily to the pregnant or lactating mother. All amounts specified herein as administered "per day" or a "daily dose" or "daily amount" may be delivered in one unit dose or in two or more doses administered over the course of a 24 hour period., preferably in one dose.

The probiotic can be administered alone (e.g. pure or diluted in water or milk, for example) or, preferably, in a mixture or composition with other compounds, including, for example, dietary or nutritional supplements, prebiotics, medicines, carriers, flavours, etc.

The terms "nutritional supplement" or "dietary supplement" or "food supplement" as used herein refers to a substance or a composition that provides nutrients to an individual that may otherwise not be consumed in sufficient quantities by said individual.

Vitamins and minerals are non-limiting examples of dietary supplements that can be included in the composition as taught herein. Non-limiting examples of vitamins that may be particularly useful for administration to a pregnant or lactating mother include provitamins A, B1, B2, B3, B5, B6, B12, C, D3, E, folic acid, biotin and any mixture thereof. The composition as taught herein may further comprise minerals and/or trace elements such as, without limitation, iron, magnesium, copper, manganese, zinc, selenium, chrome, molybdenum, iodine and nay mixtures thereof. Any source or form of minerals suitable for ingestion by the pregnant or lactating mother may be used such as, without limitation, a mineral salt such as zinc chloride, zinc picolinate, zinc sulfate, zinc oxide, zinc acetate, zinc carbonate, and combinations of the foregoing.

The composition as taught herein may advantageously further comprise a source of omega-3 fatty acids such as alpha-linolenic acid (ALA), eicosapentaenoic acid (EPA) and/or docosahexaenoic acid (DHA), in any suitable amount as known by the person skilled in the art, for example in an amount of 100 to 500 mg per daily dose, more preferably between 200 and 400 mg per daily dose.

Other compounds that may be present in the composition as taught herein include prebiotics. A "prebiotic" means a non-digestible food ingredient that beneficially affects the host by selectively stimulating the growth and/or activity of one or a limited number of bacteria in the digestive tract that can improve the health of the host. Any prebiotic known in the art can be included in the composition as taught herein. Non-limiting examples of prebiotic compounds include oligosaccharides, fructo-oligosaccharides, galacto-oligosaccharides, xylo-oligosaccharides, inulin or its derivatives, lactulose or of its derivatives, mannan-oligosaccharides, or any combination thereof. In certain embodiments, the composition as taught herein is a synbiotic composition comprising a probiotic as taught herein and at least one prebiotic. As used herein, the term "synbiotic" refers to a combination of a probiotic and a prebiotic. Advantageously, said combination may provide for a synergistic effect on the health of the host.

Optionally, the composition as taught herein may comprise at least one additional probiotic, said additional probiotic may be chosen from the group consisting of: *Archaea, Firmicutes, Bacteroidetes, Proteobacteria, Actinobacteria, Verrucomicrobia, Fusobacteria, Metanobacteria, Spirochaetes, Fibrobacters, Deferribacteres, Deinococcus, Thermus, Cyanobacteria, Methanobrevibacterium, Lactobacillus, Peptostreptococcus, Ruminococcus, Coprococcus, Subdolingranulum, Dorea, Bulleidia, Anaerofustis, Gemella, Roseburia, Catenibacterium, Dialister, Anaerotruncus, Staphylococcus, Micrococcus, Propionibacterium, Enterobacteriaceae* (non-pathogenic), *Faecalibacterium, Bacteroides, Parabacteroides, Prevotella, Eubacterium, Akkermansia, Bacillus, Butyrivibrio*, and *Clostridium*, or any combination thereof. The composition as taught herein may also comprise at least one strain of fungus and/or yeast, said fungal and/or yeast strain may be chosen from *Saccharomyces, Candida, Pichia, Debaryomyces, Torulopsis, Aspergillus, Rhizopus, Mucor*, or *Penicillium*.

The composition may also comprise a source of carbohydrates, a source of protein and/or a source of fat.

Dietary protein may be preferred as a source of protein. Any suitable dietary protein may be added, for example, animal proteins or peptides (such as milk proteins (e.g. casein and whey proteins), or meat proteins), vegetable proteins or peptides (such as soy proteins, wheat proteins, rice proteins or pea proteins), a mixture of free amino acids, or any combination thereof.

Lipid making up the fat source may be any suitable fat or fat mixture. Vegetable fat may be particularly suitable, for example soy oil, palm oil, coconut oil, safflower oil, sunflower oil, corn oil, canola oil, lecithin and the like. Animal fat such as milk fat may also be added.

A source of carbohydrate may be added to the composition as taught herein. Any suitable carbohydrate, including a monosaccharide, an oligosaccharide, a polysaccharide, or any mixture thereof, may be used for addition to the composition. Non-limiting examples of carbohydrates include sucrose, lactose, glucose, fructose, corn syrup solids, maltodextrin, or a mixture thereof. Dietary fibre may also be added. The dietary fibre may be from any suitable origin, including for example soy, pea, oat, pectin, guar gum, acacia gum, fructo-oligosaccharide or a mixture thereof.

One or more food grade emulsifiers may be included in the composition; for example diacetyl tartaric acid esters of mono- and di-glycerides, lecithin and mono- or di-glycerides or a mixture thereof. Similarly, suitable salts and/or stabilisers may be included.

Also flavours, including sweeteners such as sugar, corn syrup, fructose, dextrose, maltodextrose, cyclamates, saccharin, phenyl-alanine, xylitol, sorbitol, maltitol, and herbal sweeteners such as *Stevia*, for example, may be added to the composition as taught herein to provide taste variations.

The daily doses the compounds administered with the probiotic should always comply with the published safety guidelines and regulatory requirements Skilled artisans will be able to determine appropriate dosages.

The composition comprising the probiotic and optionally one or more other compounds as described herein may be a food composition or a nutritional composition, in particular a maternal food composition or a maternal nutritional composition. A "food composition" or a "nutritional composition" as used herein means a composition that satisfies at least a portion of an individual's nutrient requirements. As used herein a "maternal" nutritional composition or food composition refers to a nutritional composition or food composition designed to help meeting the specific nutritional requirements of women during pregnancy and/or lactation.

The nutritional composition may be provided, for example, as a food product, in particular a functional food product, a food ingredient, or a nutritional supplement.

The term "food product", as used herein, refers to any kind of product that may be safely consumed by a human or animal. The term "functional food product" or "nutraceutical" as used herein, refers to a food product providing an additional health-promoting or disease-preventing function to the individual. Said food product or functional food product may be, for example, a cereal based-product, a drink, a bar, a yoghurt, a cookie, a cracker, milk, a chewable tablet, etc. The term "food ingredient" as used herein refers to a composition that is added to a food product to achieve a desired effect.

The composition as taught herein may also be a pharmaceutical composition. The pharmaceutical composition may also comprise other substances, such as an inert vehicle, or pharmaceutically acceptable adjuvants, carriers, preservatives etc., which are well known to persons skilled in the art. The term "pharmaceutically acceptable" as used herein is consistent with the art and means compatible with the other ingredients of a pharmaceutical composition and not deleterious to the recipient thereof. The excipients that may be used in the pharmaceutical composition is not particularly limited and may therefore be one or more excipients selected from the group consisting of: an active pharmaceutical ingredient excipients, binder excipients, carrier excipients, co-processed excipients, coating system excipients, controlled release excipients, diluent excipients, disintegrant excipients, dry powder inhalation excipients, effervescent system excipients, emulsifier excipients, lipid excipients, lubricant excipients, modified release excipients, penetration enhancer excipients, permeation enhancer excipients, pH modifier excipients, plasticiser excipients, preservative excipients, preservative excipients, solubilizer excipients, solvent excipients, sustained release excipients, sweetener excipients, taste making excipients, thickener excipients, viscosity modifier excipients, filler excipients, compaction excipients, dry granulation excipients, hot melt extrusion excipients, wet granulation excipients, rapid release agent excipients, increased bioavailability excipients, dispersion excipients, solubility enhancement excipients, stabiliser excipients, capsule filling excipients, or any combination hereof. A skilled person is aware that use of such media and agents for pharmaceutical active substances is common practice and incorporation of these excipients is hence well known in the art. It is evident that all of the used ingredients should be non-toxic in the concentration contained in the final pharmaceutical composition and should not negatively interfere with the activity of the probiotic, said probiotic preferably being present in the pharmaceutical composition as the predominant pharmaceutically active ingredient.

In certain embodiments, the probiotic; and optionally the at least one additional probiotic and/or the additional fungal and/or yeast strain as described elsewhere herein are encapsulated in a carrier phase, thereby forming microencapsulated probiotic particles, to preserve the metabolic activity of the probiotics upon passage through the gastrointestinal tract. The carrier phase may comprise at least one substance selected from the group consisting of alginate, chitosan, pectin, pullulan, gelatin, carrageenan, agar or a combination thereof. Preferably, said at least one substance is a hydrocolloid. The carrier phase further comprises at least one nutritious source as described elsewhere herein (e.g. one or more of a monosaccharide, a polysaccharide, an aminoacid, a peptide, a protein, a vitamin, a yeast extract, a halogen salt of an alkali or earthalkali metal, an antioxidant, glycerol, zinc acetate, zinc chloride, zinc lactate, ascorbic acid, citric acids or a vegetable oil and milk fat). Preferably, the microencapsulated probiotic particles further comprise an external coating (e.g. alginate, chitosan, pectin, pullulan, gelatine, carageenan, agar, cellulose, hemicelulose, ethylcellulose, carboxymethylcellulose and their mixture).

Processes for the manufacture of microencapsulated probiotics are known from the prior art. For example, WO2012098239 discloses a process comprising the following steps:

- mixing a preparation of living probiotic microorganisms and a carrier phase, which carrier phase further comprises at least as nutritious source and optionally other components of the composition as taught herein,
- extruding the mixture of said living probiotic microorganisms and said carrier phase to produce microspheres,
- collecting said microspheres into a bath containing a solidification solution, and optionally
- encapsulating the extruded mixture, with an external coating.

The extrusion step may be performed at a predetermined speed of liquid flow of 0.2 to 5 m/s through at least one vibrating nozzle in a laminar flow drip casting (e.g. using a vibrational support), said vibrating nozzle may have a vibration frequency in a range of 1 to 20000 Hz, a vibration amplitude of at least 0.5 μm and the vibration may preferably be orientated in an axial or a lateral direction with respect to the flow to generate droplets. Alternatively, two liquids may be extruded in a laminar flow with one or multiple double nozzle systems comprising an inner nozzle and an outer nozzle.

The compositions as taught herein may be in the form of solid, semi-solid or liquid formulations or alternatives thereof. Examples of solid formulations include, but are not limited to tablets, enterocoated tablets, enterocoated capsules, globules, capsules, orosoluble capsules, softgel capsules, sachets, chewing gums, dusts, granules and powders which may be wettable, spray-dried or freeze-dried. Examples of liquid formulations include, but are not limited to, aqueous, organic or aqueous-organic solutions, suspensions and emulsions.

By way of example, if a composition as taught herein is used in a tablet form—e.g. for use as a food supplement—the tablets may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycolate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included. Non-limiting examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like.

When a pharmaceutical composition as taugh therein is a solid formulation it may be formulated e.g., as a tablet, a sucking tablet, a sweet, a chewing tablet, a chewing gum, a capsule, a sachet, a powder, a granule, a coated particle, a coated tablet, an enterocoated tablet, an enterocoated capsule, a melting strip or a film. When the pharmaceutical composition is a liquid formulation it may be formulated as an oral solution, a suspension, an emulsion or syrup. Said pharmaceutical composition may further comprise a carrier material such as, without limitation, oat meal gruel, lactic acid fermented foods, resistant starch, dietary fibres, carbohydrates, proteins, and glycosylated proteins.

These tablets and equivalent solid dosage forms may be prepared by any suitable means, which have been described in detail in the art (e.g. for pharmaceutical compositions: Kaur, Processing technologies for pharmaceutical tablets: A review, Int Res J Pharm, 2012).

Intranasal administration of a composition as taught herein can be accomplished using a nasal spray, a nasal wash solution or direct application within the nose.

Administration of a composition as taught herein to the lung could be in the form of a dry powder, inhaled using an inhaler device. The formulation may also be in the form of an aerosol. The aerosol may be a solution, suspension, spray, mist, vapour, droplets, particles, or a dry powder, for example, using a method dose inhaler including HFA propellant, a metered dose inhaler with non-HFA propellant, a nebulizer, a pressurized can, of a continuous sprayer.

A further aspect of the invention relates to compositions such as food compositions or pharmaceutical compositions as described elsewhere herein comprising an effective amount of the probiotic as taught herein for use in any of the indications disclosed herein such as the prevention or treatment of a viral respiratory infection in a subject.

A further aspect of the invention relates to use, in particular non-therapeutic use, of a probiotic as taught herein as a supplement in a maternal diet, particularly in a maternal diet prior to pregnancy, during pregnancy and/or during lactating, preferably during pregnancy and/or during lactating. In preferred embodiments, said probiotic is comprised in a composition such as a food composition or a pharmaceutical composition as described elsewhere herein.

A related aspect is directed to a composition such as a food composition or a pharmaceutical composition as described elsewhere herein comprising an effective amount of the probiotic as taught herein for maternal administration. In preferred embodiments, the maternal administration comprises prior to pregnancy, during pregnancy, and/or during lactating, preferably during pregnancy and/or during lactating.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

The herein disclosed aspects and embodiments of the invention are further supported by the following non-limiting examples.

EXAMPLES

Material and Methods

Mice

C57BL/6 mice were purchased from ENVIGO (Zeist, Netherlands). Mice were housed and bred in a specific pathogen-free animal facility in individually ventilated cages with a controlled day-night cycle and given food and water ad libidum. All experiments were approved by the institutional Animal Care and Local Use Committee. During the experimental time, mice were housed in an infectious animal facility in individually ventilated cages with the same conditions as in the previous animal facility.

Murine Maternal Probiotic Supplementation

The $15^{th}$ day of gestation (i.e. 6 days before delivery), pregnant C57BL/6 females (10-12 weeks) were orally administrated daily with *Lactobacillus rhamnosus* VES001 (*L. rhamnosus;* $2 \cdot 10^8$ CFU) or *Bifidobacterium lactis* VES002 (*B. lactis;* $2 \cdot 10^8$ CFU)/100 µl of NaCl 0.9% (B. Braun, Melsungen, Deutschland). The treatment was maintained until three days post-delivery at the rate of one daily gavage.

Neonatal Murine Model of Influenza a Infection

Three-days-old mice, slightly anesthetised with inhaled isoflurane, were infected intranasally (i.n) with 0.25 PFU (0.36 $TCID_{50}$) of influenza virus H1N1 strain PR8 (A/Puerto Rico/8/34) in a 5 µl volume. The viral stock used for those experiments was created from the infection of Madin-Darby canine kidney cells (MDCKs; ATCC). Virus titers were determined by two methods: the Tissue Culture Infection Dose ($TCID_{50}$) and the resazurin assay. The viral stock was stored in aliquots at −80° C. and when defrost the rest of the aliquot was discarded to avoid freeze-defreeze cycles. Analyses of the infected lungs were done at 3-6-9 days post-infection (dpi).

Influenza a Replication

At 3/6/9 days post-infection, the lungs of the neonates were harvested, weighted and frozen at −80° C. RNA was isolated from the entire lungs by the Nucleospin™ RNA Plus kit (Macherey Nagel) according to the manufacturer's protocol. RNA samples were quantified using the Nanodrop™ spectrometer and stored at −20° C. Reverse transcription and qPCR were performed in a single step using the TaqMan RNA Amplification on the Lightcycler® 480 apparatus (Roche). Virus was measured by qPCR using the PR8 (A/Puerto Rico/8/34) specific primers. RT-qPCR assays were performed with the RNA virus master kit (Roche): 4 µl of RT qPCR mix n°2 (5×), 0.1 µl of RT enzyme solution n°1 (200×), 1 µl of influenza A virus sense primer (6 µM) (5'-AAGACCAATCCTGTCACCTCTGA-3' (SEQ ID NO:1)), 1 µl of influenza A virus antisense primer (6 µM) (5'-CAAAGACCAATCCTGTCAGTCC-3' (SEQ ID NO:2)) and 1 µl of influenza A virus probe (4 µM) (FAM-5'-TTTGTGTTCACGCTCACCGT-3' (SEQ ID NO:3)-TAMRA). For viral load measurement, a standard curve was developed with a serial 10-fold dilutions of PR8 stock with a known PFU concentration. Ct values were plotted against virus quantity in PFU per milliliter. Ct values were converted to PFU. Virus RNA quantities in lungs were expressed as PFU/100 mg lung.

Real-Time Quantitative PCR from Frozen Tissues

Lungs were harvested, weighted and frozen at −80° C. RNA was extracted using the RNA Plus NucleoSpin® following the manufacturer's protocol (Machery-Nagel; Düren, Germany). Reverse transcription and qPCR were performed in a single step using the TaqMan RNA Amplification on Lightcycler® 480 equipment (Roche; Machelen, Belgium). RNA quantification was obtained using the NanoDrop 1000 Spectrophotometer (Thermo Scientific) and samples were all diluted at 100 ng/µl. Moreover, Hypoxanthine Phosphoribosyltransferase (HPRT) and Peptidylprolyl isomerase A (PPIA) were used as housekeeping genes to normalize mRNA levels between samples. The list of designed primers for the detection cytokines/chemokines can be found in Table 1.

TABLE 1

Primers and probes for the detection of cytokines/chemokines.

| Gene | Forward primer | Reverse primer | Probe |
|---|---|---|---|
| m-PPIA | TCCTGGCATCTTGTCCATGG (SEQ ID NO: 7) | TTGCCATCCAGCCATTCAGT (SEQ ID NO: 8) | TGCTGGACCAAACACAAACGGCGGTTCCCA (SEQ ID NO: 9) |
| m-HPRT | GGACCTCTCGAAGTGTTGGAT (SEQ ID NO: 10) | CCAACAACAAACTTGTCTGGAA (SEQ ID NO: 11) | CAGGCCAGACTTTGTTGGATTTGAA (SEQ ID NO: 12) |
| m-IFNγ | GGATGCATTCATGAGTATTGC (SEQ ID NO: 13) | GCTTCCTGAGGCTGGATTC (SEQ ID NO: 14) | TTTGAGGTCAACAACCCACAGGTCCA (SEQ ID NO: 15) |
| m-Cxcl9 | GAACCCTAGTGATAAGGAATGCA (SEQ ID NO: 16) | CTGTTTGAGGTCTTTGAGGGATT (SEQ ID NO: 17) | CATCAGCACCAGCCGAGGCACG (SEQ ID NO: 18) |
| m-Cxcl10 | GCCGTCATTTTCTGCCTCAT (SEQ ID NO: 19) | GCTTCCCTATGGCCCTCATT (SEQ ID NO: 20) | TCTCGCAAGGACGGTCCGCTG (SEQ ID NO: 21) |
| m-Eomes | CCTTCACCTTCTCAGAGACACAGTT (SEQ ID NO: 22) | TCGATCTTTAGCTGGGTGATATCC (SEQ ID NO: 23) | TCGCTGTGACGGCCTACCAAAACA (SEQ ID NO: 24) |

For individual samples, relative RNA levels ($2^{-\Delta\Delta Ct}$) were determined by comparing a) the cycle thresholds (Ct) for the gene of interest and calibrator gene (ΔCt), the geomean of HPRT and PPIA and b) $2^{-\Delta Ct}$ values for the experimental group vs. the reference sample ($2^{-\Delta Ct}$ values mean of the non-infected neonates at 3 days-old).

Flow Cytometry

Neonatal mediastinal lymph nodes (MLNs) were dissociated using microscope slides while infected lungs were collected at specific time point (3/6/9 dpi) in RPMI-1640 medium supplemented with recombinant Grade I DNAse I (10 U/ml, Thermo Fisher) and collagenase A (1 mg/ml, Roche). Dissociation was done using the GentleMACS (Miltenyi Biotec; Bergisch Gladbach, Germany) performing the Program Lung 1 and 2 with an incubation at 37° C. for 20 min between both steps. To lyse erythrocytes, Ammonium-Chloride-Potassium lysing Buffer (ACK) was added to cell suspensions for 1 min. For extracellular staining, cells of interest were stained with antibody mix diluted in FACS buffer (PBS/0.5% BSA/2 Mm EDTA) at 4° C. in the dark for 20 minutes. To exclude dead cells, fixable viability dye conjugated to iFluor860 maleimide (AAT Bioquest; California, USA) was used.

For intracellular staining for the TFs, cells from the lungs were fixed and permeabilized using the Foxp3-Staining buffer kit (eBiosciences) following the one-step manufacturer protocol.

For intracellular staining for the cytokines, cells from the lungs were cultured in RPMI-1640 medium containing 10% (vol/vol) FCS, 2 mM glutamine, 1 mM sodium pyruvate, 0.1 mM non-essential amino acids and 40 mM b-mercaptoethanol (Lonza; Basel, Switzerland). Different types of stimulation were done depending on the cells of interest:

Innate cells (3 dpi)

Cells cultures ($2\cdot10^6$/ml) were restimulated with 5 ng/ml of PMA and 500 ng/ml (Sigma-Aldrich) for 4 hours with 1 μg/ml of GolgiPlug™ (Brefeldin A; Bd Biosciences, California, United States). Cells were fixed and permeabilized using the BD Fixation/Permabilization kit following the manufacturer protocol.

Virtual memory CD8 T cells (6 dpi)

Cells cultures ($2\cdot10^6$/ml) were restimulated with 10 ng/ml of rIL-12 (PEPROTech) and 10 ng/ml of rIL-18 (MBL, Nagoya, Japan) for 4 hours with 1 μg/ml of GolgiPlug™ added during the last two hours (Brefeldin A; Bd Biosciences, California, United States). Cells were fixed and permeabilized using the BD Fixation/Permabilization kit following the manufacturer protocol.

IAV-specific CD8+ T cell response (9 dpi)

Cells cultures ($2\cdot10^6$/ml) were restimulated with 2 μM PA224-233 peptide (Kaneka Eurogentec S.A., Seraing, Belgium) for 4 hours with 1 μg/ml of GolgiPlug™ (Brefeldin A; Bd Biosciences, California, United States). Cells were fixed and permeabilized using the BD Fixation/Permabilization kit following the manufacturer protocol.

Antibodies used for flow cytometry are listed in Table 2.

TABLE 2

Antibodies used for flow cytometry experiments.

| Markers | Fluorochrome | Clone | Company | Dilution |
|---|---|---|---|---|
| CD11a | APC | 2D7 | BD Pharmingen ™ | 1/200 |
| CD11b | Alexa Fluor ® 700 | M1/70 | BD Pharmingen ™ | 1/200 |
| CD11c | BV421 | N418 | BD Horizon ™ | 1/200 |
| CD11c | PE-Cy ™7 | HL3 | BD Pharmingen ™ | 1/200 |
| CD103 | BV421 | M290 | BD Horizon ™ | 1/200 |
| CD103 | R718 | M290 | BD OptiBuild ™ | 1/200 |
| CD127 | PE-Cy ™7 | SB/199 | BD Pharmingen ™ | 1/200 |
| CD172a | BV480 | P84 | BD OptiBuild ™ | 1/500 |
| CD19 | FITC | 1D3 | BD Pharmingen ™ | 1/500 |
| CD26 | BV786 | H194-112 | BD OptiBuild ™ | 1/200 |
| CD3e | FITC | 145-2C11 | BD Pharmingen ™ | 1/500 |
| CD3e | PE-CF594 | 145-2C11 | BD Horizon ™ | 1/500 |
| CD4 | PE-Cy TM7 | RM4-5 | BD Pharmingen ™ | 1/200 |
| CD44 | BUV395 | IM7 | BD OptiBuild ™ | 1/200 |
| CD45 | BV510 | 30-F11 | BD Horizon ™ | 1/500 |
| CD45 | PE-CF594 | 30-F11 | BD Horizon ™ | 1/500 |
| CD49d | BV711 | R1-2 | BD OptiBuild ™ | 1/200 |
| CD62L | BV421 | MEL-14 | BD Horizon ™ | 1/200 |
| CD8 α | APC-H7 | 53-6.7 | BD Pharmingen ™ | 1/200 |

TABLE 2-continued

Antibodies used for flow cytometry experiments.

| Markers | Fluorochrome | Clone | Company | Dilution |
|---|---|---|---|---|
| CXCR3 | APC | CXCR3-173 | BD Pharmingen ™ | 1/200 |
| Eomes | PE | Da11mag | eBioscience ™ | 1/200 |
| F4/80 | PE | BM8 | BioLegend ® | 1/500 |
| IFNγ | PE | XMG1.2 | BD Pharmingen ™ | 1/200 |
| I-A/I-E | BV711 | M5/114.15.2 | BD Horizon ™ | 1/500 |
| Ly6C | PerCP-Cy ™5.5 | HK1.4 | BioLegend ® | 1/200 |
| LY6G | APC-H7 | 1A8 | BD Pharmingen ™ | 1/500 |
| NK1.1 | FITC | PK136 | BD Pharmingen ™ | 1/500 |
| PDCA1 (CD317) | BV650 | 927 | BioLegend ® | 1/200 |
| TNFα | R718 | MP6-XT22 | BD Horizon ™ | 1/200 |
| XCR1 | APC | ZET | BioLegend ® | 1/200 |

Samples were acquired on CytoFLEX LX (6 lasers, Beckman Coulter) and analyzed using FlowJo Software (Tree Star, Inc).

Statistical Analysis

Data are expressed as mean+/−SEM. Statistical comparison was done using GraphPad Prism 8 (GraphPad Software; San Diego, USA). Shapiro-Wilk test was used for normality test of the data and to choose the appropriate statistical test. P values less than or equal to 0.05 were considered significant.

Example 1: Impact of Maternal Supplementation with VES001 or VES002 on the Viral Loads in Neonatal Lungs Pregnant C57BL/6 female mice (10-12 weeks) were orally administrated daily with $2\cdot10^8$ CFU *Lactobacillus rhamnosus* VES001 or $2\cdot10^8$ CFU *Bifidobacterium lactis* VES002 from the 15th day of gestation (i.e. 6 days before delivery) until three days post-delivery. Control mice were not supplemented with probiotic. Their 3-days old offspring were infected with 0.25 PFU of influenza virus H1N1 strain PR8. At 3, 6 or 9 days post-infection, viral load in the lungs was measured.

FIG. 1 shows that maternal supplementation with *Lactobacillus rhamnosus* VES001 or *Bifidobacterium lactis* VES002 controlled influenza viral replication in the lungs of the offspring.

*B. lactis* maternal supplementation inhibited earlier the viral loads into the neonatal lungs of the pups at 3 days post-infection (3 dpi) whereas the *L. rhamnosus* maternal supplementation inhibited the viral replication at 6 dpi compared to infected neonates from untreated mothers (FIG. 1).

Example 2: Maternal *L. rhamnosus* or *B. lactis* Supplementation Modifies Antigen Presenting Cell Recruitment in the Lungs and the Draining Lymph Nodes of IAV Infected Neonates In the very early phase of the infection, antigen presenting cells (APCs) such as type 1 conventional dendritic cells (cDC1) and plasmacytoid dendritic cells (pDCS) are the cells at the interface between the innate and the adaptative immune response. Indeed, those APCs play an important role in the regulation of antiviral CD8 cytotoxic T-cell (CTLs) responses that lead to viral clearance. cDC1 are well documented to be effective cross-presenters to CD8 T cells of viral antigens from surrounding infected epithelial cells whereas pDC have been demonstrated to produce antiviral type I interferon during IAV infection.

Figure 2:
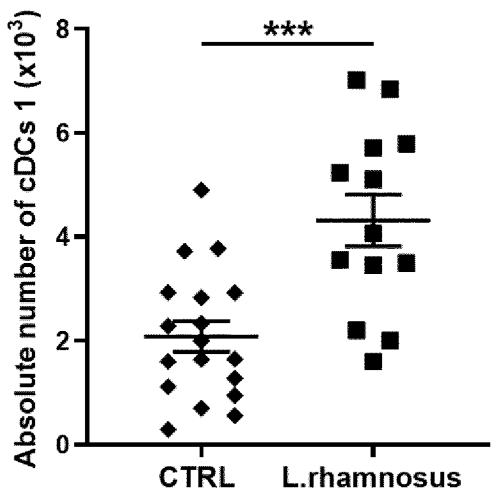
FIG. 2. Impact of the maternal supplementation with *L. rhamnosus* or *B. lactis* on the recruitment of APCs to the lungs at 3 days-old. cDC 1 (CD45+, CD64−, Lin−, MHCII+, CD11c+, CD26+, XCR1+, SIRPα−) counts were determined in the lungs of 3 days-old neonates born from untreated control (CTRL) or *L. rhamnosus* (A) or *B. lactis* (B) treated mothers by flow cytometry. Results represent 2 experiments and are shown as mean±SEM. Statistical significance was determined by an unpaired t test (parametric) or a Mann-Whitney test (no parametric). ***p<0.001
Figure 2:
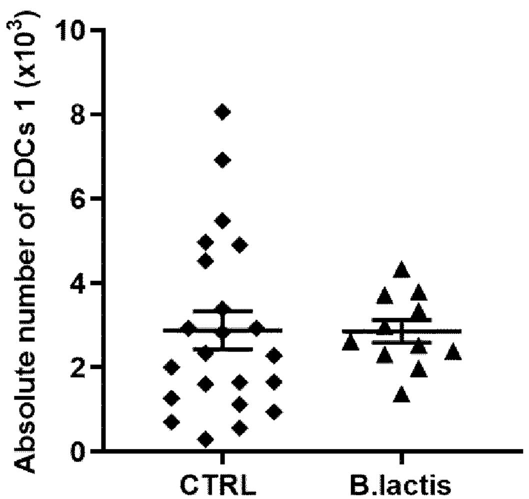

The impact of maternal *L. rhamnosus* or *B. lactis* supplementation on the lung distribution of those cDC1 and pDCs was evaluated. At steady state, it was already observed that the *L. rhamnosus* maternal supplementation increased the number of cDCs 1 into the lungs of their pups at 3 days-old compared to pups from untreated-mothers (FIG. 2A) while the *B. lactis* supplementation didn't alter their number (FIG. 2B).

During the first hours of infection, migratory cDCs 1 (CD103+) process the IAV antigens into peptides fragments that are displayed on their membrane through their major histocompatibility complex (MHC). Then, during the cDC1 activation process, these cells migrate from the infected lungs to the draining mediastinal lymph node (MLN) to cross-present exogenous antigens through their MHCI to naïve CD8+ T cells to become effector cytotoxic T cells (CTLs). This process has been described altered during the neonatal period (Ruckwardt et al. (2014) PLOS Pathog. Doi: 10.1371/journal.ppat.1003934).

Figure 3:
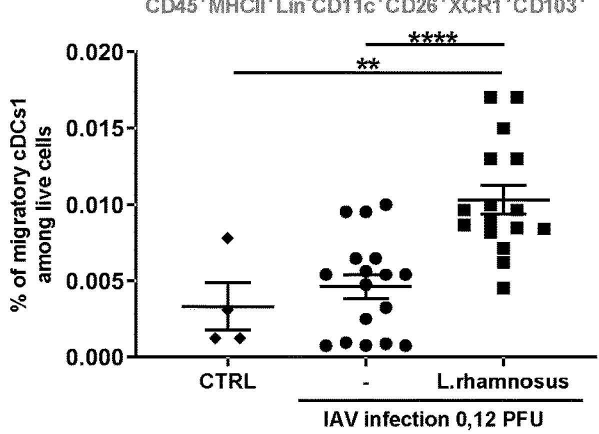
FIG. 3. Impact of the maternal supplementation with *L. rhamnosus* or *B. lactis* on the recruitment of APCs to the mediastinal lymph nodes during IAV infection. Cells from the lymph nodes (migratory type 1 conventional dendritic cells (cDCs 1; CD45+, Lin−, MHCII+, CD11c+, CD26+, XCR1+, CD103+), resident cDCs 1 (CD45+, Lin−, MHCII+, CD11c+, CD26+, XCR1+, CD8+) and plasmacytoid dendritic cells (pDCs, CD45+, Lin−, MHCII+, CD11c+/−, CD26+, PDCA1+ LYC+) of uninfected neonates (CTRL n=4), or neonates infected with influenza A from mothers not supplemented with probiotics (IAV n=17), or supplemented with *L. rhamnosus* (IAV+*L. rhamnosus* n=16) (A-C) or *B. lactis* (IAV+*B. lactis* n=8) (D-F) were analyzed by flow cytometry at 3 dpi. *L. rhamnosus* graphs represent a pool of 3 experiments, *B. lactis* graphs represent a pool of 2 experiments and shown as mean±SEM. Statistical significance was determined by a one-way ANOVA (Holm-Sidak's multiple comparisons test) or a Kruskall Wallis (Dunn's multiple comparisons test). *p<0.05 p<0.005 *p<0.001 ****p<0.0001
Figure 3:
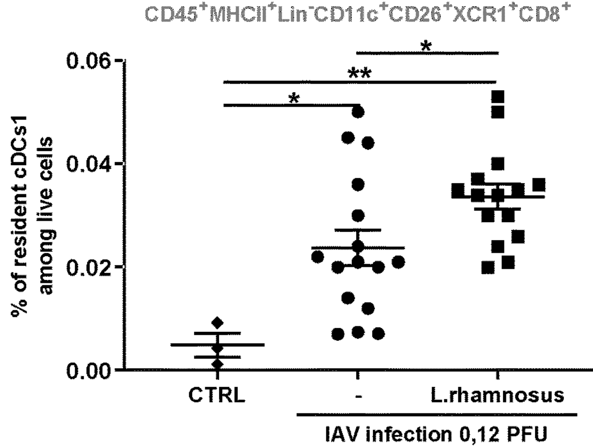
Figure 3:
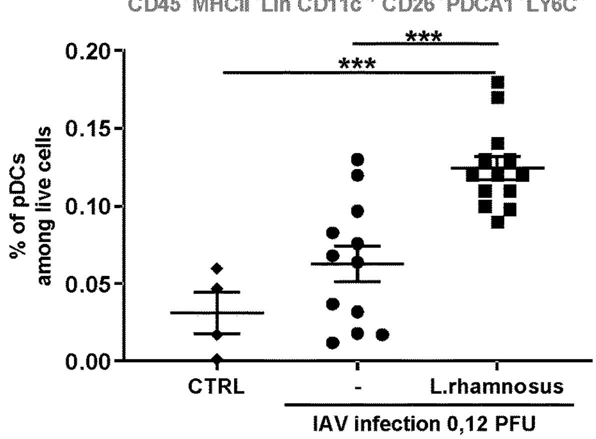
Figure 3:
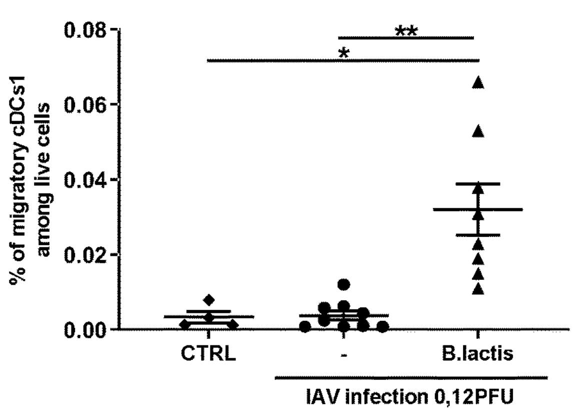
Figure 3:
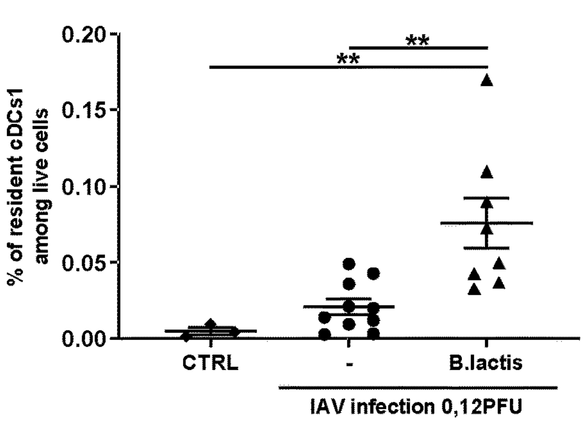
Figure 3:
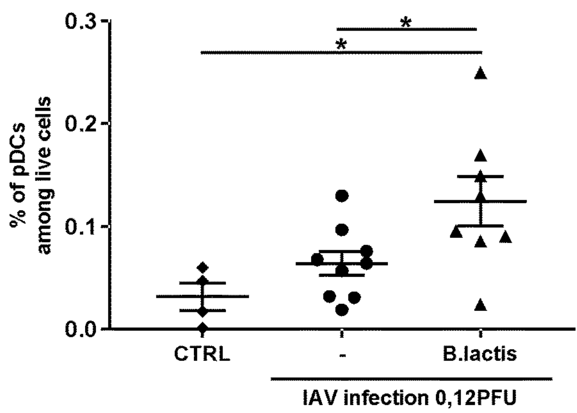

Maternal *L. rhamnosus* (FIG. 3A) or *B. lactis* (FIG. 3D) supplementation increased the migration of CD103+ cDC1 into the MLNs at 3 dpi compared to infected neonates from untreated mothers.

Also the migration of other APCs to the MLNs was evaluated such as the resident CD8+ cDCs 1 (cDCs found only in the lymphatic system) and pDCs. Resident cDCs 1 have been shown to activate memory CD8+ T cells and to maintain the antigen presentation into the MLNs at later time points during infection. pDCs are known to be important in the production of antiviral type I interferon cytokines and chemoattractants for the accumulation of T cells into the lungs. Moreover, pDCs can migrate to the MLNs to induce differentiation of B cells into antibody-secreting plasma cells.

At 3 dpi, a greater migration of resident cDCs 1 and pDCs was observed to the MLNs of infected neonates whose mothers received the *L. rhamnosus* (FIG. 3B-C) or *B. lactis* (FIG. 3E-F) supplementation compared to infected neonates from CTRL mothers.

Overall, the data show an increased capacity of neonatal cDC1 and pDC to migrate to lymphoid organs upon IAV infection when their mothers have been supplemented with *L. rhamnosus* or *B. lactis.*

Example 3: Maternal *L. rhamnosus* or *B. lactis* Supplementation Increases the Level of IFNγ-Producing IAV-Specific Effector CD8+ T Cells in IAV Infected Neonates The induction and regulation of virus-specific CD8 T-cell responses which are directly linked to the recruitment of cDC1 in lymphoid organs are essential for the clearance of IAV.

As a higher level of neonatal cDC1 into the MLNs upon IAV infection was obserbed while there is a maternal L. *Rhamnosus* or *B. lactis* supplementation (Example 2), the level of virus-specific CD8 T cells and their synthesis of IFN-γ cytokine in the MLNs was evaluated.

IFN-γ is known as a potent antiviral cytokine that can enhance the cytotoxicity of other immune cells, promote further activation of DCs and inhibit IAV replication in infected cells. In adults, the activation and recruitment of experienced effector CD8+ T cells are around 7 dpi; however, studies have demonstrated a delay in this virus-specific response early in life (Lines et al. 2010 J. Immunol. Doi: 10.4049/jimmunol.0903075; Fike et al. 2019 Journal of Leukocyte Biologydoi: 10.1002/JLB.5RU0319-105R). In view hereof, the specific-IAV CD8+ T cell response was studied at 9 dpi.

To observe an increased production of IFN-γ by the experienced-effector CD8+ T cells (CD8+ T cells that have been cross presented with a specific-IAV peptide by the cDCs 1), the cells were stimulated for 4 hours with one of the dominant antigenic peptides: polymerase acidic protein (PA).

Figure 4:
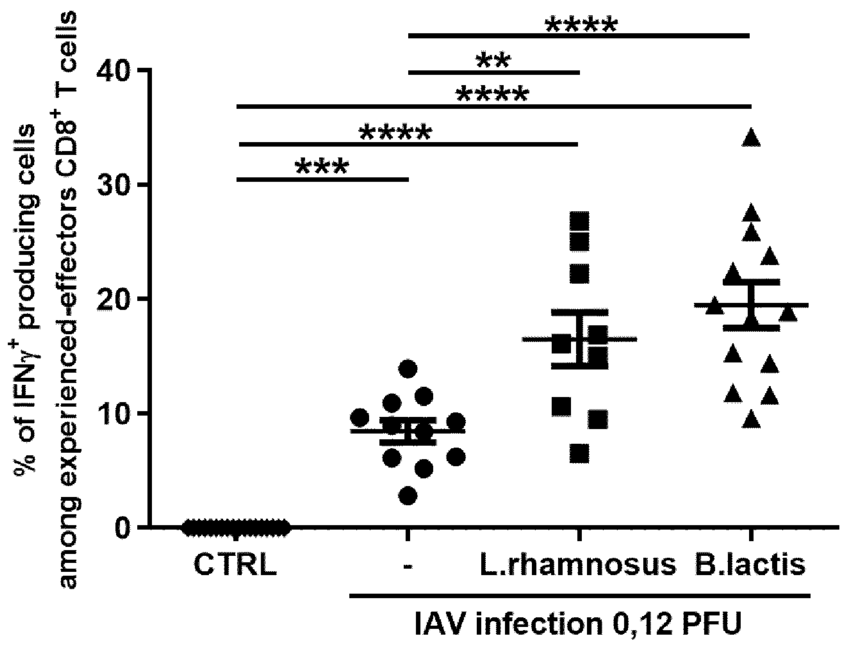
FIG. 4. Impact of the maternal supplementation with *L. rhamnosus* or *B. lactis* on the IAV-specific effector CD8+ T cells producing IFNγ in the infected neonatal lungs. IFNγ+ experienced-effector CD8+ T cells (CD45+ CD3+ CD4− CD8+ CD62L− CD44+ CD11a+ CD49d+ IFNγ+) from the lungs of uninfected neonates (CTRL n=18), or neonates infected with influenza A from mothers not supplemented with probiotics (IAV n=11), or supplemented with *L. rhamnosus* (IAV+*L. rhamnosus* n=9) or *B. lactis* (IAV+*B. lactis* n=13) were analyzed by flow cytometry at 9 dpi after 4 hours stimulation with one of the IAV peptide: polymerase acidic protein (PA). The graph represents a pool of 3 experiments. Statistical significance was determined by a Two-way ANOVA (Holm-Sidak's multiple comparisons test). *p<0.05 p<0.005 *p<0.001 ****p<0.0001

The percentage of specific-IAV effector CD8+ T cells that produced IFN-γ was increased in the lungs of neonates whose mothers received either the *L. rhamnosus* or *B. lactis* supplementation compared to infected neonates (FIG. 4).

Example 4: Maternal *L. rhamnosus* Supplementation Increases an Early Response of Innate-Like CD8+ T Cells in IAV Infected Neonates Neonatal adaptative T cells have historically been considered as immature or defective. Today, new subsets of neonatal T cells endowed with innate-like features are described. They are equipped to quickly develop into effector cells to confer immune protection against pathogens. Therefore, effector pro-inflammatory cytokines and chemokines that would be produced in the lung of IAV infected neonates before the development of the adaptative T cells were studied.

Figure 5:
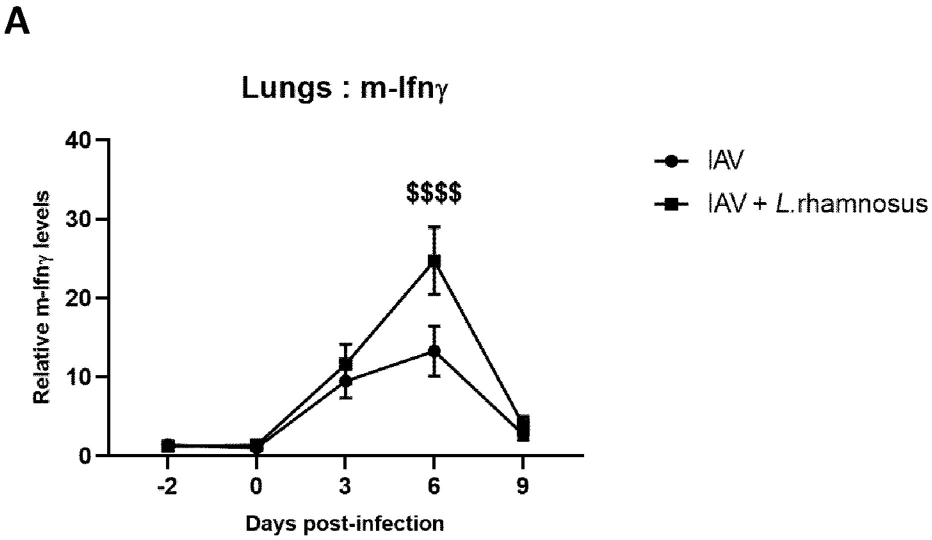
FIG. 5. Impact of the maternal supplementation with *L. rhamnosus* on the production of pro-inflammatory chemokines in the infected neonatal lungs. Pulmonary relative mRNA expression of Ifnγ, CXCL9, CXCL10 and Eomes were analyzed by quantitative RT-PCR (qRT-PCR). Relative unit was obtained by comparing each group to the mean of non-infected neonatal mice. A. Ifnγ: 1-day-old uninfected neonates (CTRL) (−2 days post-infection) IAV group (n=9) and IAV+*L. rhamnosus* group (n=8); 3-days-old uninfected neonates (0 days post-infection) IAV group (n=12) and IAV+*L. rhamnosus* group (n=13), 3 days post-infection (DPI) IAV n=9, 3 DPI IAV+*L. rhamnosus* n=10, 6 DPI IAV n=16, 6 DPI IAV+*L. rhamnosus* n=12, 9 DPI IAV n=9, 9 DPI IAV+*L. rhamnosus* n=6. B. CXCL9: 1-day-old CTRL uninfected (−2 days post-infection) IAV n=9 and IAV+*L. rhamnosus* n=8, 3-days-old CTRL uninfected (0 days post-infection) IAV n=12 and IAV+*L. rhamnosus* n=13, 3 DPI IAV n=11, 3 DPI IAV+*L. rhamnosus* n=10, 6 DPI IAV n=15, 6 DPI IAV+*L. rhamnosus* n=11, 9 DPI IAV n=10, 9 DPI IAV+*L. rhamnosus* n=6. C. CXCL10: 1-day-old CTRL uninfected (−2 days post-infection) IAV n=9 and IAV+*L. rhamnosus* n=7, 3-days-old CTRL uninfected (0 days post-infection) IAV n=11 and IAV+*L. rhamnosus* n=13, 3 DPI IAV n=11, 3 DPI IAV+*L. rhamnosus* n=9, 6 DPI IAV n=15, 6 DPI IAV+*L. rhamnosus* n=12, 9 DPI IAV n=9, 9 DPI IAV+*L. rhamnosus* n=6. D. Eomes: 1-day-old CTRL uninfected (−2 days post-infection) IAV n=9 and IAV+*L. rhamnosus* n=8, 3-days-old CTRL uninfected (0 days post-infection) IAV n=5 and IAV+*L. rhamnosus* n=3, 3 DPI IAV n=10, 3 DPI IAV+*L. rhamnosus* n=8, 6 DPI IAV n=16, 6 DPI IAV+*L. rhamnosus* n=12, 9 DPI IAV n=11, 9 DPI IAV+*L. rhamnosus* n=9. Statistical significance was determined by a Two-way ANOVA (Holm-Sidak's multiple comparisons test). $^{\$\$}p<0.005$ $^{\$\$\$\$}p<0.0001$ FIG. 6. Impact of the maternal supplementation with *L. rhamnosus* on the production of IFNγ, TNFα and the expression of Eomes on CXCR3+ virtual memory (VM) CD8+ T cells in the infected neonatal lungs. A. CXCR3+ VM CD8+ T cells (CD45+ CD3+ CD4− CD8+ CD62L+ CD44+ CD49d− CXCR3+ IFNγ+) from the lungs of uninfected neonates (CTRL) (n=5), or neonates infected with influenza A from mothers not supplemented with probiotics (IAV n=7), or supplemented with *L. rhamnosus* (IAV+*L. rhamnosus* n=8) were analyzed by flow cytometry at 6 dpi after 4 hours Il-12/Il-18 stimulation. B. CXCR3+ VM CD8+ T cells (CD45+ CD3+ CD4− CD8+ CD62L+ CD44+ CD49d− CXCR3+ TNFα+) from the lungs of CTRL n=5, IAV n=7, IAV+*L. rhamnosus* n=6 were analyzed by flow cytometry at 6 dpi after a 4 hours culture with Brefeldin A. C. CXCR3+ VM CD8+ T cells (CD45+ CD3+ CD4− CD8+ CD62L+ CD44+ CD49d− CXCR3+ Eomes+) from the lungs of CTRL n=4, IAV n=7, IAV+*L. rhamnosus* n=6 were analyzed by flow cytometry at 6 dpi. Graphs represent one experiment. Statistical significance was determined by a One-way ANOVA (Holm-Sidak's multiple comparisons test). *p<0.05 p<0.005 *p<0.001 ****p<0.00001
Figure 5:
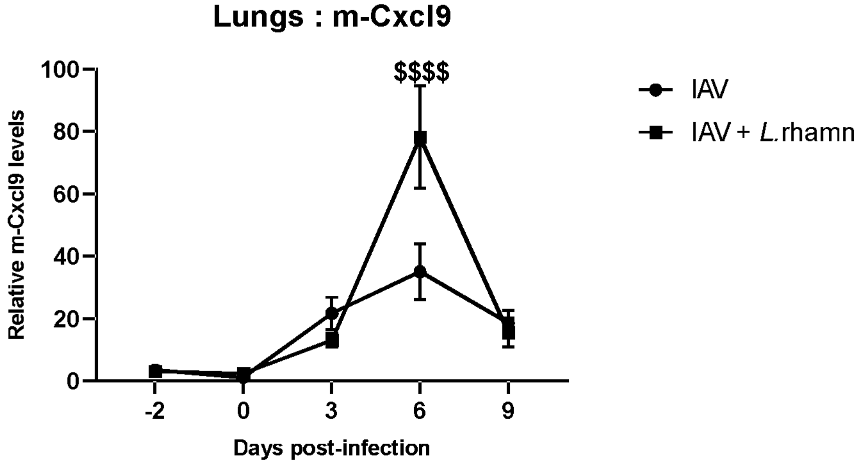
Figure 5:
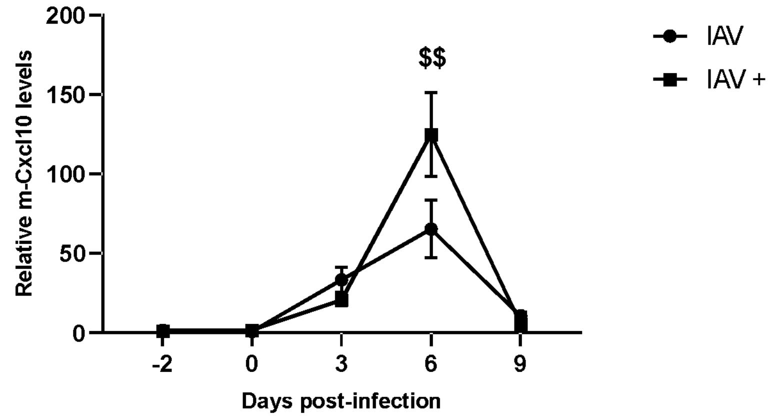
Figure 5:
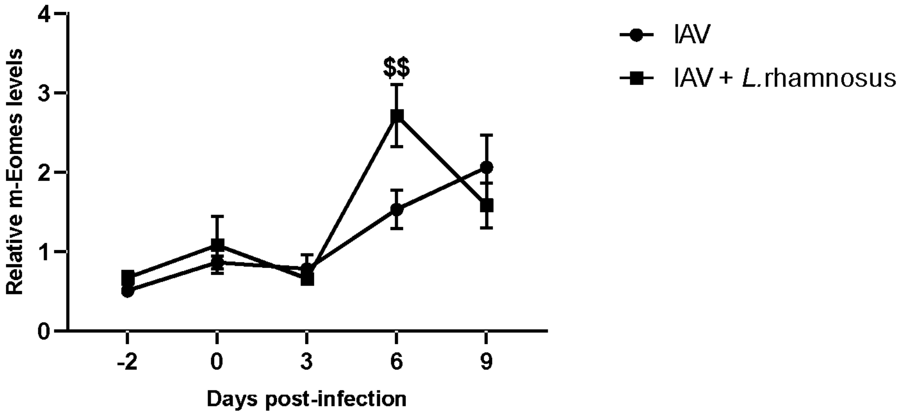

An increased m-Ifnγ transcription into the neonatal lungs of maternal *L. rhamnosus* supplementation group was observed compared to infected neonates alone at 6 dpi (FIG. 5A). This pro-inflammatory cytokine increase was associated with the increase of two chemokines (CXCL9 FIG. 5B and CXCL10 FIG. 5C) that help to attract other immune cells that possess the CXCR3 receptor like natural killers (NKs) or CD8+ T cells. Also an increase in the RNA messenger of Eomes was observed in the maternal *L. rhamnosus* supplemented group after the infection at 6 dpi compared to maternal unsupplemented group (FIG. 5D).

In view of the observed increase of two chemokines (CXCL9/CXCL10) and the increase in the TF Eomes in the neonatal infected lungs of the maternal *L. rhamnosus*-supplementation group, a particular CD8+ T cell type was investigated: the CXCR3+ virtual memory (VM) CD8+ T cells. These cells are known to rapidly express protective effector functions in response to different inflammatory cytokines and chemokines signals without cognate antigen triggering (Lauvau & Goriely 2016 PLOS Pathog. doi: 10.1371/journal.ppat.1005722; White et al. 2017 Nature Reviews Immunology doi: 10.1038/nri.2017.34). The VM cells levels and the effector cytokines they can produce under stimulation with IL-12 and IL-18 for 4 hours were evaluated.

Figure 6:
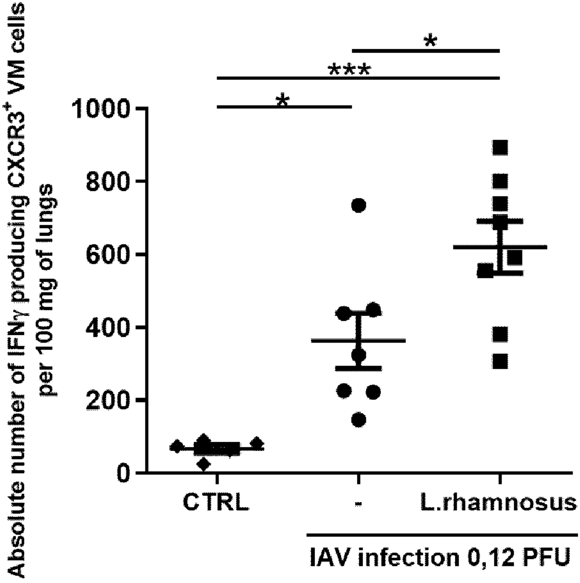
Figure 6:
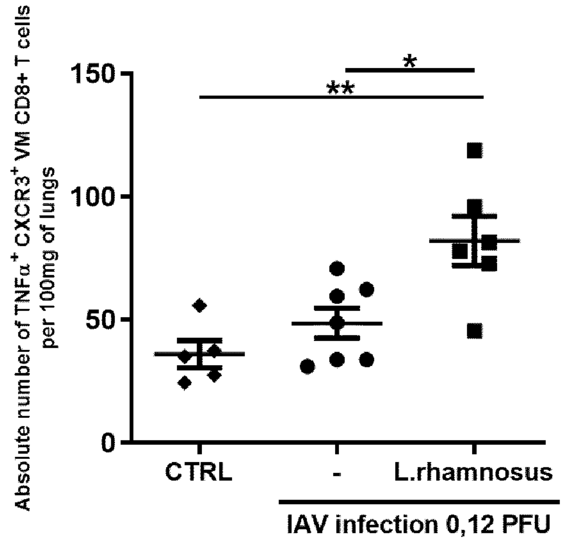
Figure 6:
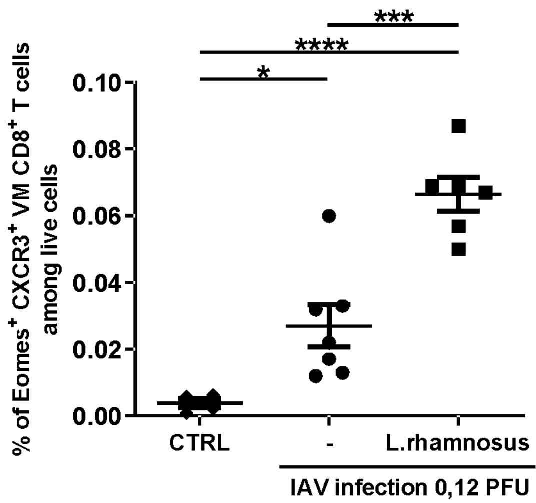

Percentages of VM cells producing either IFN-γ or TNF-α were increased at 6 dpi in the neonatal lungs of maternal *L. rhamnosus* supplemented group compared to maternal unsupplemented group (FIG. 6A-B).

Next, the increase m-RNA of the TF Eomes observed into the lungs of neonates by q-PCR was confirmed in those VM cells by flow cytometry. The percentage of CXCR3+ VM CD8+ T cells expressing Eomes was increased in the neonatal infected lungs of maternal *L. rhamnosus* supplemented group compared to maternal unsupplemented group (FIG. 6C).

Example 5: Maternal *B. lactis* Supplementation Stimulates a Very Early Response of TNF-Producing Innate Cells in the Lungs of IAV Infected Neonates Because viral loads were already lower at 3 dpi in the neonatal lungs of the maternal *B. lactis* supplemented group compared to maternal unsupplemented group (Example 1), the innate immune cells at that time into the lungs were evaluated.

The percentage of alveolar macrophages (AMs) and the percentage of NK cells were increased in the neonatal infect lungs of maternal *B. lactis* supplemented group compared to the maternal unsupplemented group (FIG. 7A-B). AMs and NKs have shown several important mechanisms responsible for the lung protection upon IAV infection.

Figure 7:
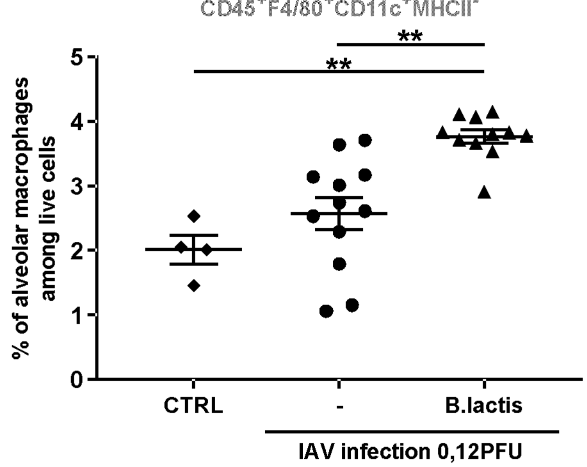
FIG. 7. Impact of the maternal supplementation with *B. lactis* on the recruitment of innate cells to the neonatal lungs during the IAV infection. Alveolar macrophages (CD45+ F4/80+ CD11c+ MHCII−) (A), natural killer (NK) cells (CD45+ CD11b+ CD11c− CD3− CD127+ NK1.1+) (B) or neutrophils (CD45+ CD11c− CD11b+ LY6G+ LY6c−) (C) from the lungs of unifected neonates (CTRL n=4), or neonates infected with influenza A from mothers not supplemented with probiotics (IAV n=12), or supplemented with *B. lactis* (IAV+*B. lactis* n=11) (A-C) were analyzed by flow cytometry at 3 days post-infection (dpi). Graphs represent a pool of 2 experiments and shown as mean±SEM. Statistical significance was determined by a one-way ANOVA (Holm-Sidak's multiple comparisons test). *p<0.05 p<0.005 *p<0.001. Alveolar macrophages (CD45+ F4/80+ CD11c+ MHCII− TNFα+) (D), natural killer (NK) cells (CD45+ CD11b+ CD11c− CD3− CD127+ NK1.1+ TNFα+) (E) or neutrophils (CD45+ CD11c− CD11b+ LY6G+ LY6c− TNFα+) (F) from the neonatal lungs of IAV n=7 or IAV+*B. lactis* n=9 (D-F) were analyzed by flow cytometry at 3 dpi after stimulation with PMA-Iono for 4 hours. Graphs represent one experiment and shown as mean±SEM. Statistical significance was determined by an unpaired t test (parametric). *p<0.05 **p<0.005
Figure 7:
Figure 7:
Figure 7:
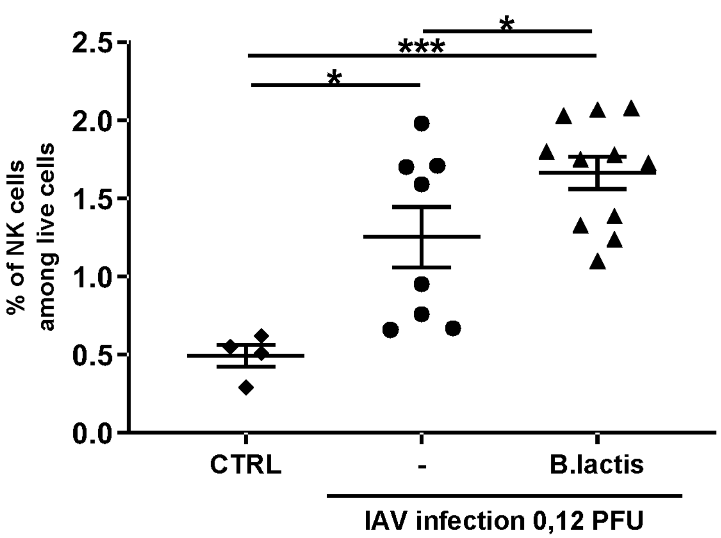
Figure 7:
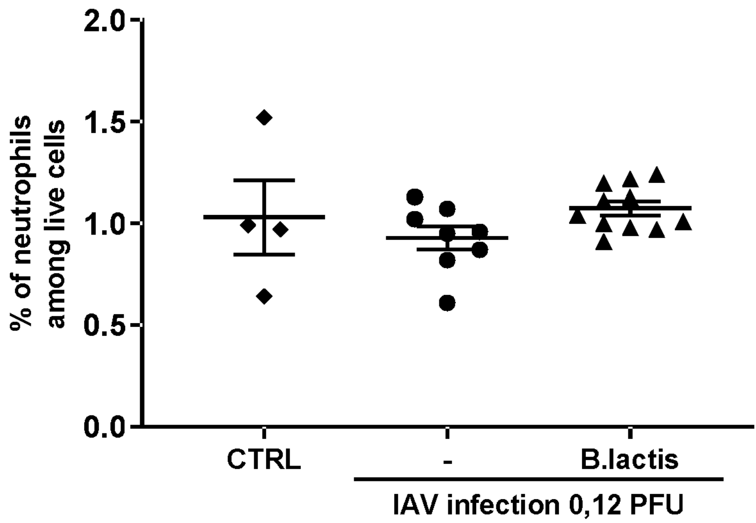
Figure 7:
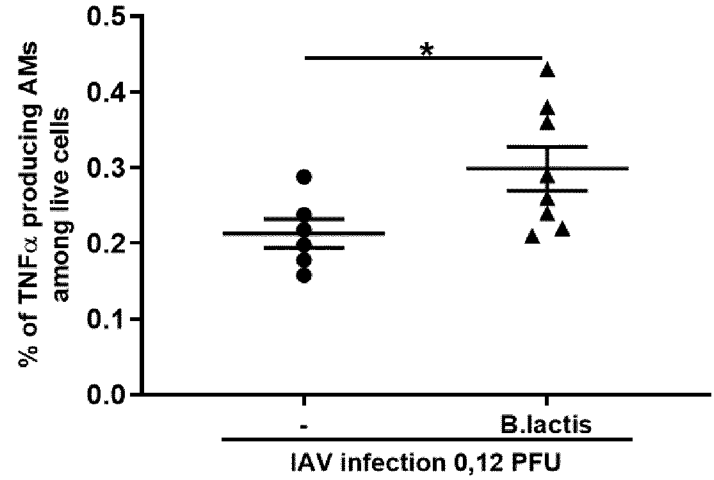
Figure 7:
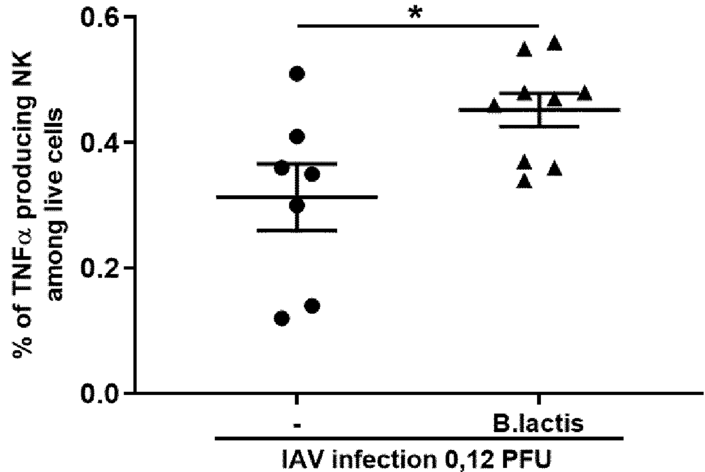
Figure 7:
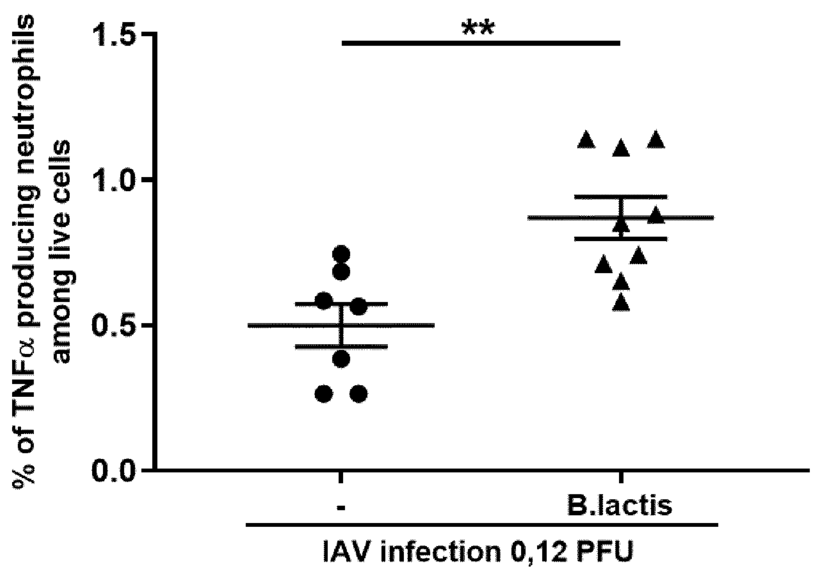

After the stimulation of those cells for 4 hours, the percentages of those AMs and NK cells that produced TNF-α were increased in the neonatal lungs of the maternal *B. lactis* supplemented group compared to the maternal unsupplemented group (FIG. 7 D-E).

Same observation was made for the neutrophils even if the percentage of those cells didn't change between the neonates from the maternal *B. lactis* supplemented group compared to the maternal unsupplemented group (FIG. 7C and FIG. 7E).

Example 6: Impact of Maternal *L. rhamnosus* VES001 Supplementation on Neonatal Murine Pneumonia Virus Infection Materials and Methods Murine Maternal Probiotic Supplementation The 11th day of gestation (i.e. 10 days before delivery), pregnant C57BL/6 females (10-12 weeks) were orally administered daily with *Lactobacillus rhamnosus* VES001 (*L. rhamnosus;* $2 \cdot 10^8$ CFU/100 μl of NaCl 0.9% (B. Braun, Melsungen, Deutschland). The treatment was maintained until three days post-delivery at the rate of one daily gavage.

Neonatal Murine Model of PVM Infection

Three-day-old mice, slightly anesthetized with inhaled isoflurane, were inoculated intranasally (i.n) with 10 PFU of murine pneumonia virus (mPVM strain 15, ATCC, USA) in a 5 μl volume.

Murine Pneumonia Virus Replication

On Apr. 7, 2010 days post-infection, the lungs of the neonates were harvested, weighted and frozen at −80° C. RNA was isolated from the entire lungs by the Nucleospin™ RNA Plus kit (Macherey Nagel) according to the manufacturer's protocol. RNA samples were quantified using the Nanodrop™ spectrometer and stored at −20° C. Reverse transcription and qPCR were performed in a single step using the TaqMan RNA Amplification on the Lightcycler® 480 apparatus (Roche). Virus was measured by qPCR using the PVM SH gene-specific primers. RT-qPCR assays were performed with the RNA virus master kit (Roche): 4 μl of RT qPCR mix n° 2 (5×), 0.1 μl of RT enzyme solution n° 1 (200×), 1 μl of PVM SH sense primer (6 μM) (5'-GCCTG-CATCAACACAGTGTGT-3' (SEQ ID NO:4)), 1 μl of PVM SH antisense primer (6 μM) (5'-GCCT-GATGTGGCAGTGCTT-3' (SEQ ID NO:5)) and 1 μl of PVM SH probe (4 μM) (FAM-5'-CGCTGA-TAATGGCCTGCAGCA-3' (SEQ ID NO:6)-TAMRA). For viral load measurement, a standard curve was developed with a serial 10-fold dilution of a standard PVM SH gene. Ct values were converted to number of copy. Virus RNA quantities in lungs were expressed as number of copy/μg lung RNA.

Statistical Analysis

Data are expressed as mean±SEM. Statistical comparison was made using GraphPad Prism 8 (GraphPad Software; San Diego, USA). Shapiro-Wilk test was used for normality test of the data and to choose the appropriate statistical test. P values less than or equal to 0.05 were considered significant.

Results

Figure 8:
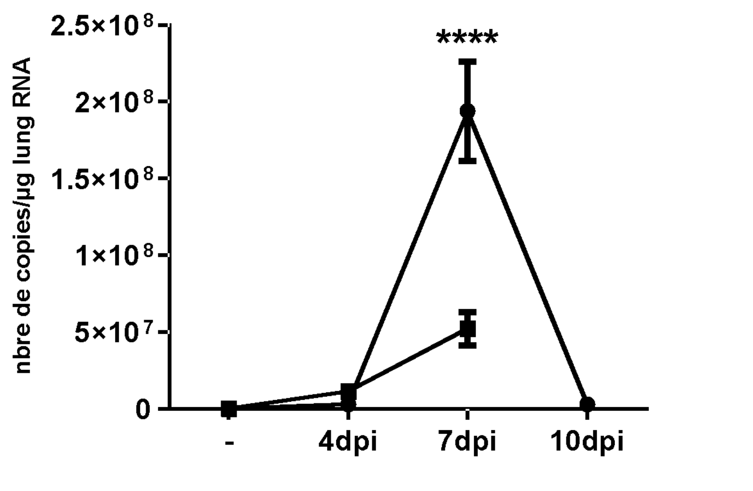
FIG. 8. Impact of the maternal supplementation with *L. rhamnosus* or *B. lactis* on the PVM viral loads in neonatal lungs. Viral load was measured in lungs of 3-days-old uninfected neonates from unsupplemented mothers (CTRL, n=10), or *L. rhamnosus* (n=10) or *B. lactis* (n=10) supplemented mothers (/), and in neonates from unsupplemented mothers (PVM), or *L. rhamnosus* (*L. rhamnosus*+PVM) or *B. lactis* (*B. lactis*+PVM) supplemented mothers at 4, 7 or 10 days post infection with PVM (4 dpi, 7 dpi, 10 dpi) (4 DPI PVM n=20, 4 DPI PVM+*L. rhamnosus* n=12, 4 DPI PVM+*B. lactis* n=23, 7 DPI PVM n=14, 7 DPI PVM+*L. rhamnosus* n=11, 7 DPI PVM+*B. lactis* n=11, 10 DPI IAV n=5). Statistical significance was determined by a Two-way ANOVA (Turkey's multiple comparisons test). *p<0.05 ****p<0.0001.

FIG. 8 shows that maternal supplementation with *Lactobacillus rhamnosus* VES001 controlled murine pneumovirus (PVM) replication in the lungs of the offspring.

The invention claimed is:

1. A composition for prevention or treatment of a viral respiratory infection in a subject, wherein the composition is administered to a pregnant or lactating mother of the subject, wherein the composition comprises a probiotic comprising at least $10^7$ cfu per dose of *Lactobacillus rhamnosus* VES001 strain deposited under accession number BCCM/LMG P 33100, and the composition is in the form of an enterocoated tablet or in the form of an enterocoated capsule.

2. The composition according to claim 1, wherein the subject is less than 6 years old.

3. The composition according to claim 1, wherein the viral respiratory infection is an influenza virus infection, a rhinovirus infection, a respiratory syncytial virus infection, a parainfluenza virus infection, a coronavirus infection or an adenovirus infection.

4. The composition according to claim 1, wherein the viral respiratory infection is an influenza virus infection.

5. The composition according to claim 1, wherein the composition is administered orally to the pregnant or lactating mother.

6. The composition according to claim 1, wherein the composition is a nutritional composition.

7. The composition according to claim 1, wherein the composition comprises the probiotic in an amount of between $1\times10^7$ cfu and $1\times10^{12}$ cfu per dose.

8. The composition according to claim 1, wherein the composition further comprises one or more of a prebiotic, a vitamin, a mineral, and an omega-3 fatty acid source.

9. The composition according to claim 1, wherein the composition is administered daily to the pregnant or lactating mother.

10. The composition according to claim 1, wherein the composition is administered to the pregnant or lactating mother for at least 4 weeks before delivery.

11. The composition according to claim 1, wherein the composition is administered to the pregnant or lactating mother for at least 1 or 2 months after delivery.

12. The composition according to claim 1, wherein the composition is administered to the pregnant or lactating mother at least during a third trimester of pregnancy and for at least 1 or 2 months after delivery when the pregnant or lactating mother is breastfeeding.

13. The composition according to claim 1, wherein the pregnant or lactating mother and the subject are human.

14. The composition according to claim 1, wherein the probiotic further comprises a *Bifidobacterium animalis* spp *lactis* strain.

15. A method for improving immunity in a subject, wherein a composition comprising an effective amount of a probiotic is administered to a pregnant or lactating mother, wherein said probiotic comprises at least $10^7$ cfu per dose of a *Lactobacillus rhamnosus* strain VES001 deposited under accession number BCCM/LMG P 33100, wherein an immunity improvement comprises:

an increase of a number of antigen presenting cells (APCs) in lungs of the subject or offspring thereof;

an increase of the number of antigen presenting cells (APCs) in lymph nodes of the subject or the offspring upon a viral respiratory infection;

an increase of a number of IFNγ-producing CD8+ T cells in lungs of the subject or the offspring upon a viral respiratory infection;

an increased synthesis of pro-inflammatory cytokines and/or chemokines in the lungs of the subject or the offspring upon a viral respiratory infection;

an increased synthesis of Eomes transcription factor in the lungs of the subject or the offspring upon a viral respiratory infection;

an increase of a number of virtual memory (VM) CD8+ T cells in the lungs of the subject or the offspring upon a viral respiratory infection;

an increase of a number of innate immune cells in the lungs of the subject or the offspring upon a viral respiratory infection;

an increase of a number of TNF-α producing innate immune cells in the lungs of the subject or the offspring upon a viral respiratory infection; or any combination thereof.

16. A composition for maternal administration comprising a probiotic, wherein said probiotic consists of at least $10^7$ cfu per dose of *Lactobacillus rhamnosus* VES001 deposited under accession number BCCM/LMG P 33100, wherein the composition comprises one or more vitamins selected from the group consisting of: provitamins A, B1, B2, B3, B5, B6, B12, C, D3, E, folic acid and biotin, and/or an omega-3 fatty acid source, and wherein the composition is in the form of an enterocoated tablet or in the form of an enterocoated capsule.

17. A method of prevention or treatment of a viral respiratory infection in an infant comprising a step of administering to a pregnant or lactating mother a probiotic supplement comprising at least $10^7$ cfu per dose of *Lactobacillus rhamnosus* VES001 deposited under accession number BCCM/LMG P 33100.

* * * * *